United States Patent [19]

Tarello et al.

[11] Patent Number: 4,518,384
[45] Date of Patent: May 21, 1985

[54] MULTIPLE MEDICAMENT CARTRIDGE CLIP AND MEDICAMENT DISCHARGING DEVICE THEREFOR

[75] Inventors: William R. Tarello, Bethesda; Claudio Lopez; Linda A. Gordon, both of Silver Spring; Thomas D. Whalen, Rockville; William B. Harvey, Olney, all of Md.

[73] Assignee: Survival Technology, Inc., Bethesda, Md.

[21] Appl. No.: 505,323

[22] Filed: Jun. 17, 1983

[51] Int. Cl.$^3$ .............................................. A61M 5/18
[52] U.S. Cl. ......................................... 604/61; 604/62
[58] Field of Search ............... 604/187, 191, 216, 232, 604/61, 62

[56] References Cited

U.S. PATENT DOCUMENTS

| | | | |
|---|---|---|---|
| 2,832,339 | 4/1958 | Sarnoff | 128/218 |
| 2,888,924 | 6/1959 | Dunmire | 604/216 |
| 3,318,021 | 5/1967 | Sarnoff | 35/17 |
| 3,380,449 | 4/1968 | Sarnoff | 128/218 |
| 3,391,695 | 7/1968 | Sarnoff | 128/218 |
| 4,004,565 | 1/1977 | Fischer et al. | 604/62 |
| 4,077,406 | 3/1978 | Sandhage et al. | 604/61 |
| 4,223,674 | 9/1980 | Fluent et al. | 604/61 |

Primary Examiner—John D. Yasko
Attorney, Agent, or Firm—Cushman, Darby & Cushman

[57] ABSTRACT

A medicament discharging device and an expendable clip thereon containing a plurality of medicament cartridges. Each of the cartridges comprises a container, a dosage of medicament in the container, a hypodermic needle sealingly contained in a sterile condition in cooperating relation with the container and a movable wall means at one end of the container operable when moved through a discharging stroke to cause the sharpened end of the needle to move outwardly out of sealingly contained relation and into the muscle tissue of a patient and the medicament dosage to move outwardly of the container into the opposite end of the needle and out of the sharpened end thereof into the muscle tissue of the patient. The medicament discharging device comprises a portable manually engageable housing structure defining a medicament cartridge receiving station, a plunger mounted in the housing structure for movement through the medicament cartridge receiving station in repetitive operative cycles each of which includes a discharging stroke in one direction and a return stroke in the opposite direction, a manually actuatable mechanism for effecting movement of the plunger through an operative cycle, and a releasable connection between the housing structure and the clip for securing the same in operative relation so that successive cartridges in the clip will be presented in the medicament cartridge receiving station of the housing structure for injection in response to an operative cycle.

41 Claims, 20 Drawing Figures

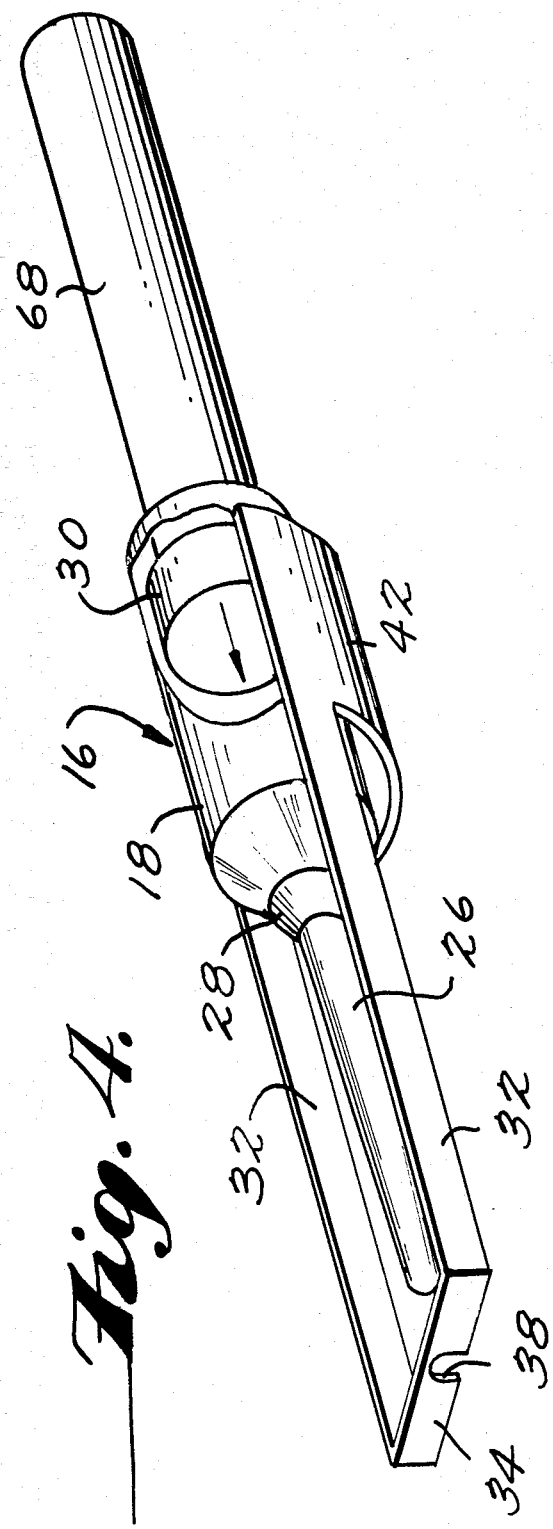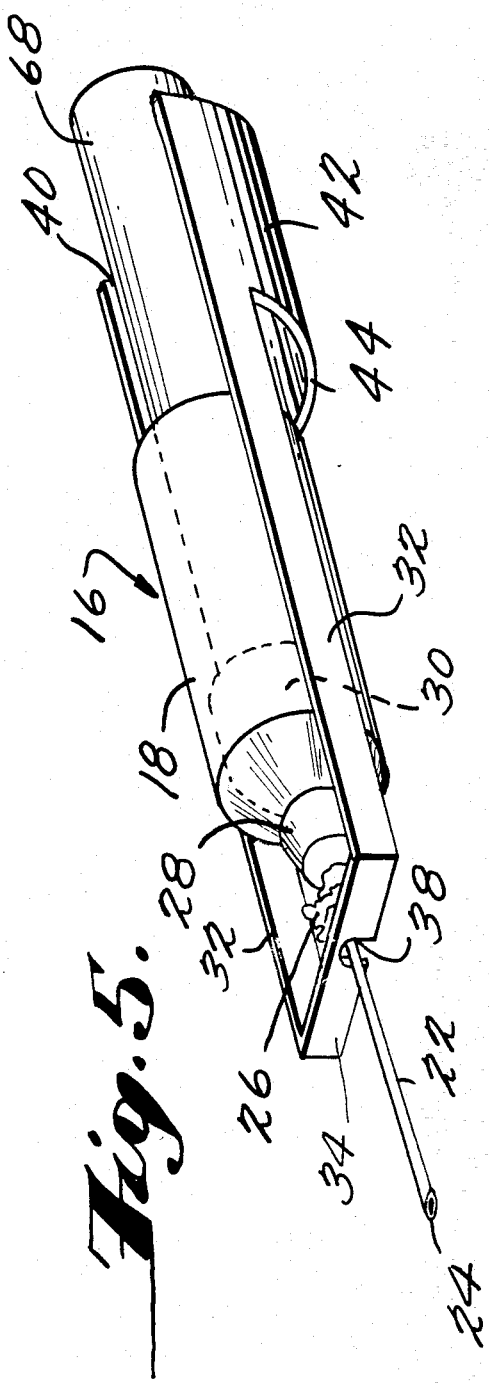

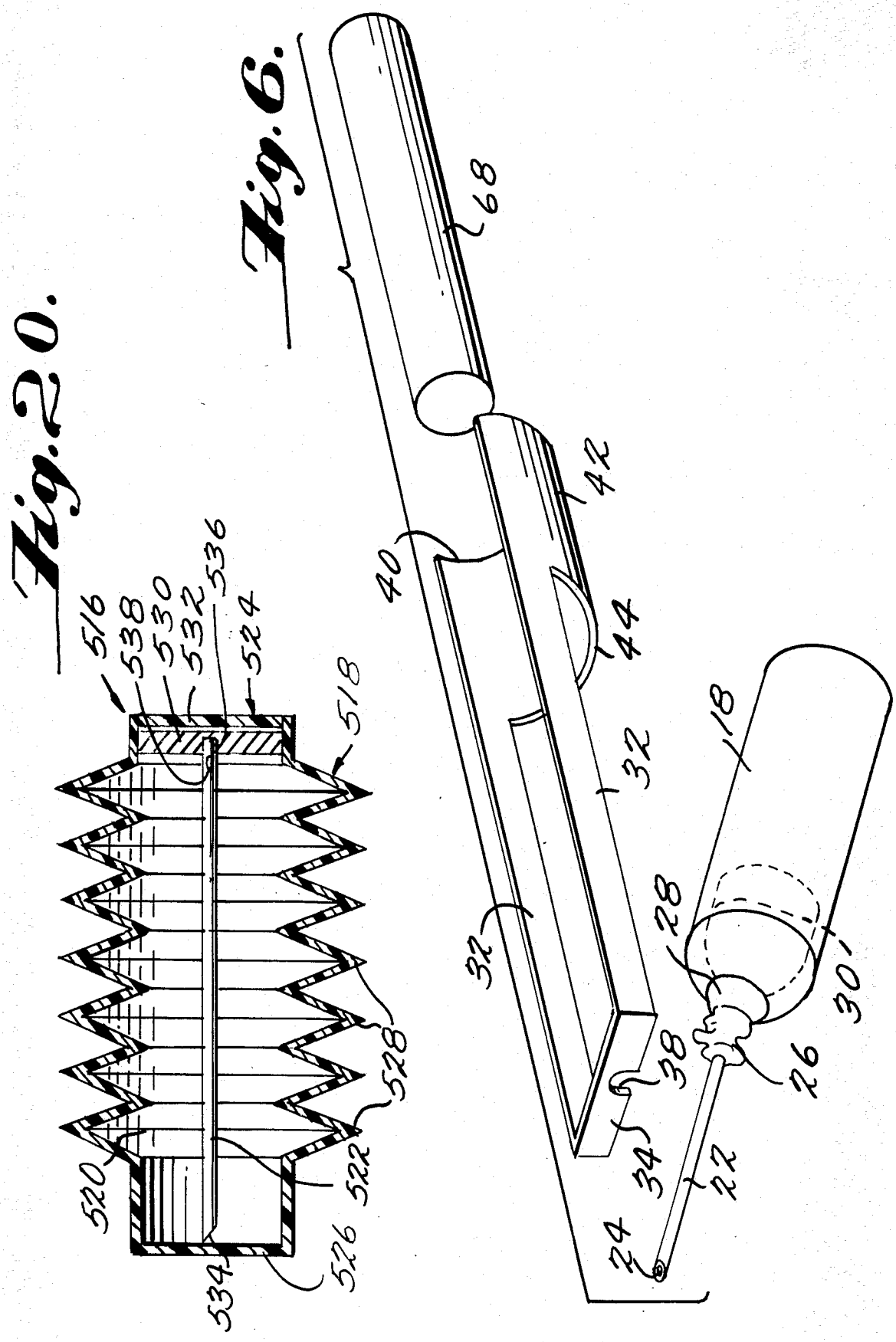

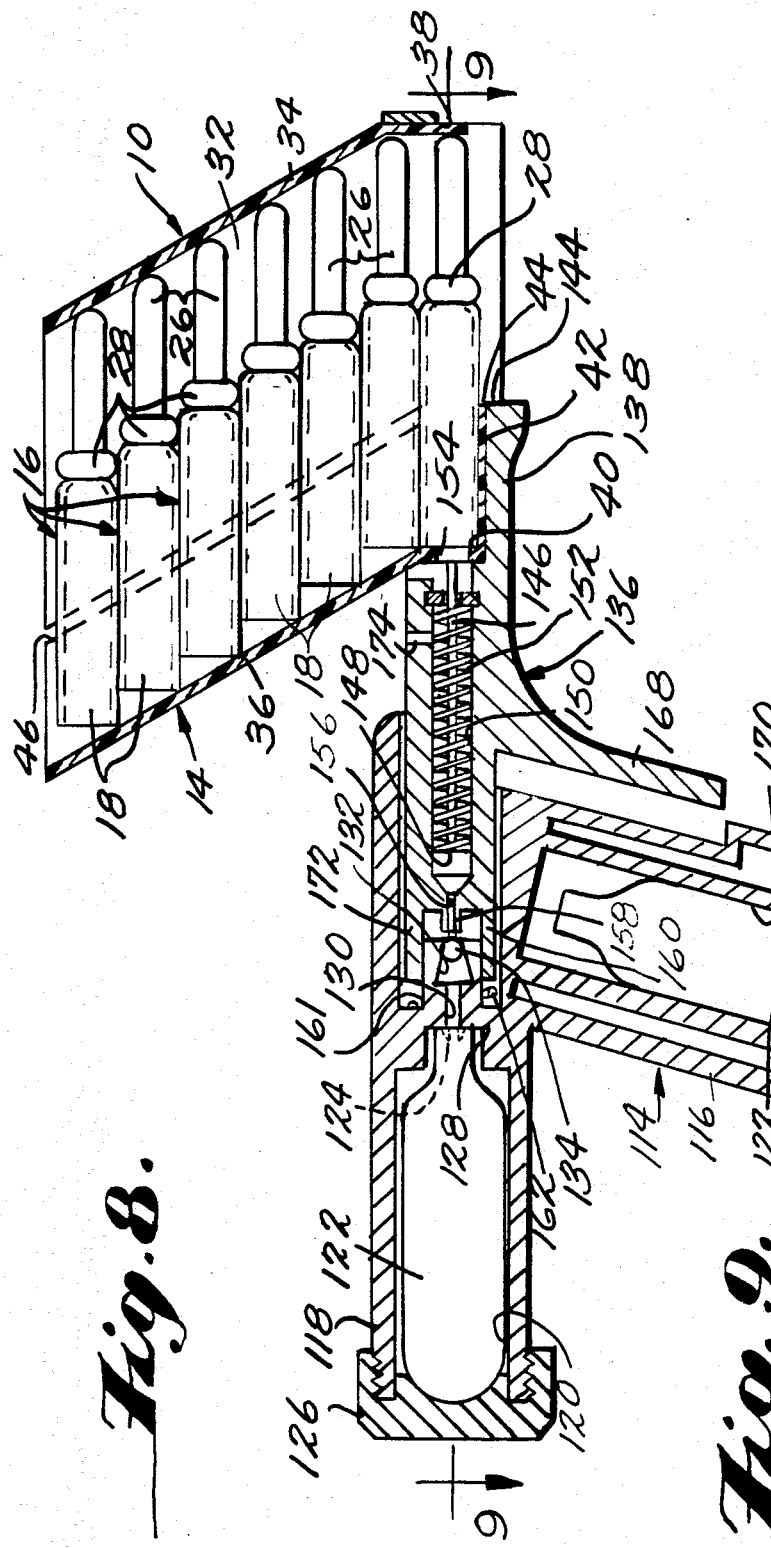
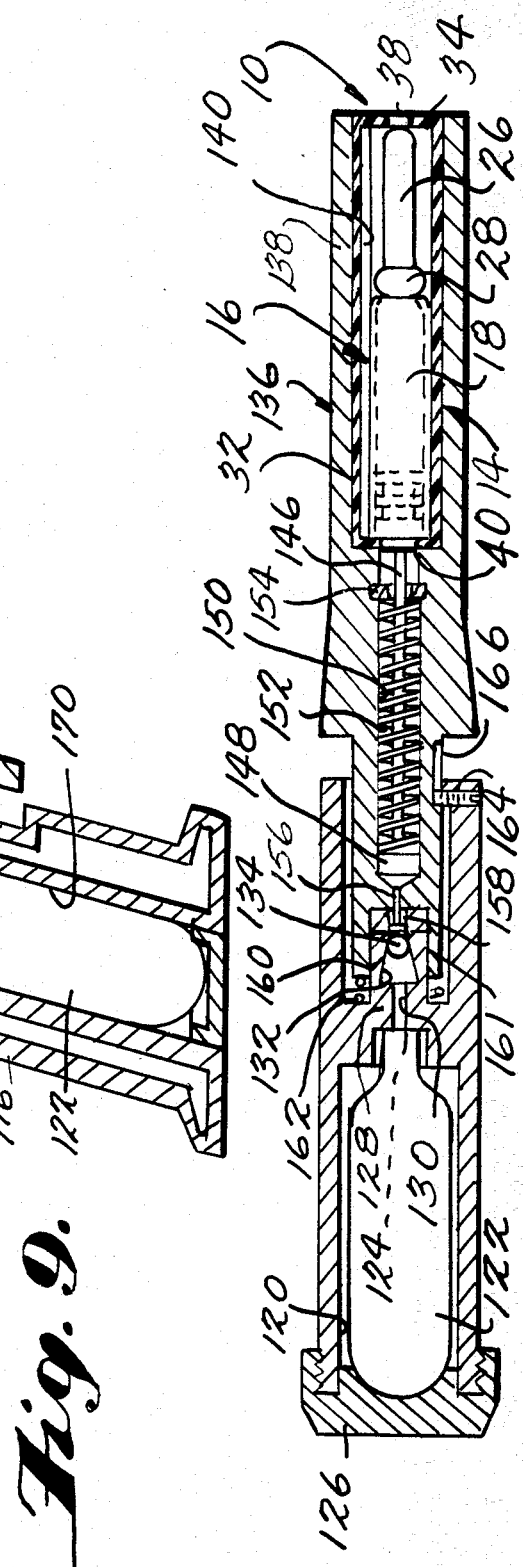
Fig. 8.
Fig. 9.

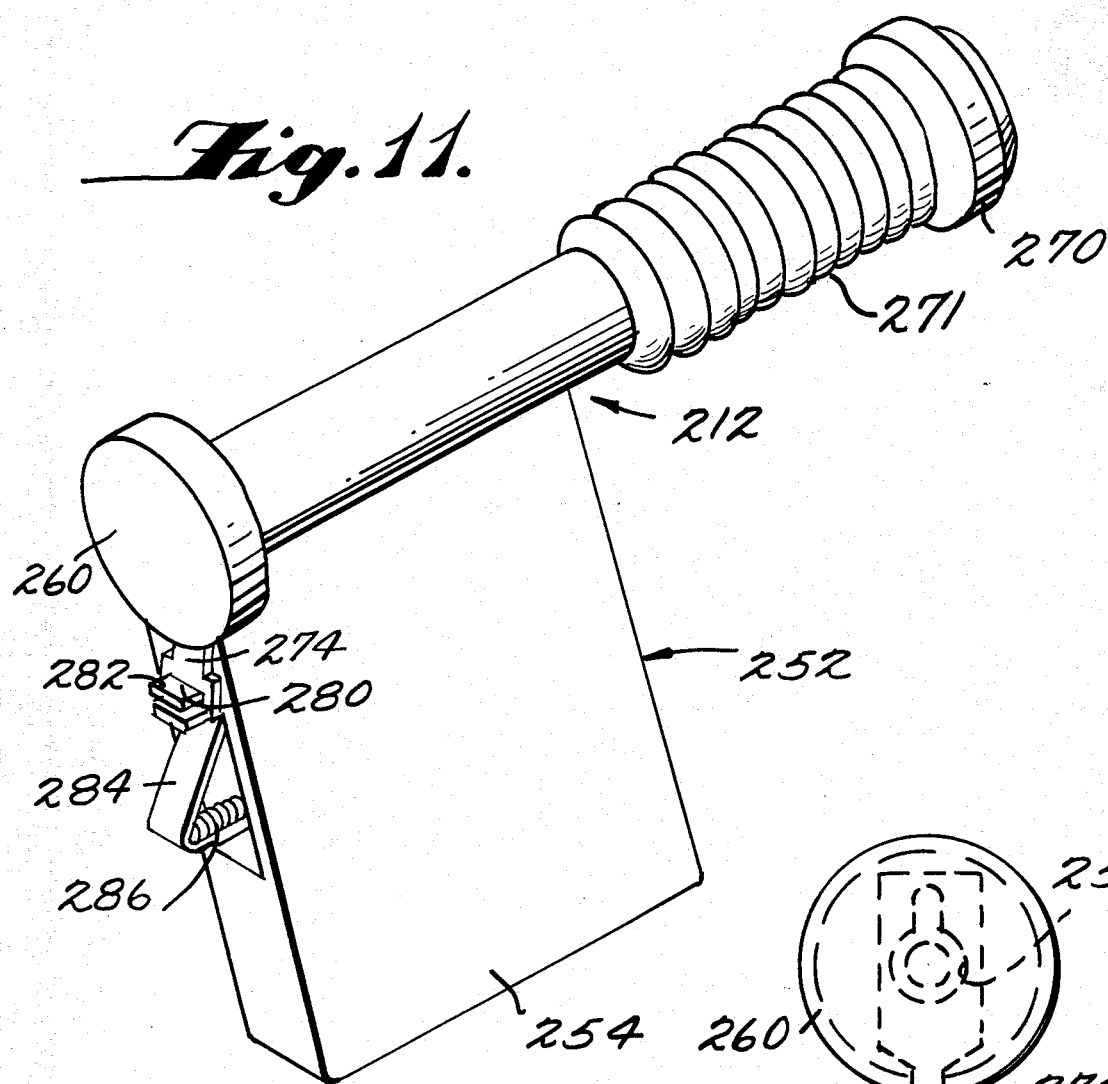
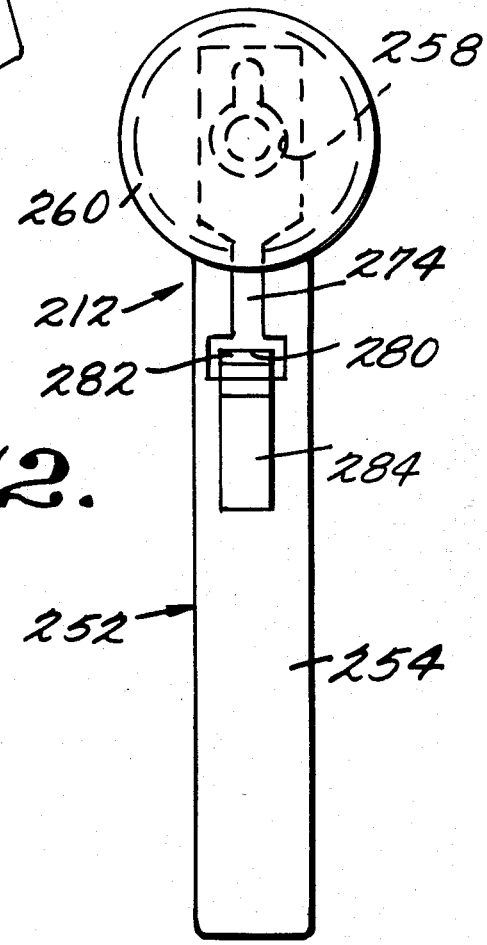

MULTIPLE MEDICAMENT CARTRIDGE CLIP AND MEDICAMENT DISCHARGING DEVICE THEREFOR

This invention relates to apparatus for injecting medicaments and to improvements in apparatus suitable for effecting multiple injections into different individuals.

There are many emergency situations presented, particularly under chemical warfare conditions, where it becomes necessary to administer a multiplicity of medicament dosages to a multiplicity of individuals as rapidly as possible and without exposing the skin areas through which the medicine dosage is injected. It is highly desirable under conditions of this nature that the procedures for effecting such rapid through-the-clothing injections should be as simple as possible.

It is an object of the present invention to provide apparatus which will meet these exacting requirements. In accordance with the principles of the present invention, this objective is obtained by providing a medicament discharging device capable of cooperatively receiving an expendable clip containing a plurality of medicament cartridges, the arrangement being such that by a single actuating procedure the medicament dosage within each successive cartridge can be discharged through the needle of the cartridge into the muscle tissue of the patient and then the discharged cartridge is removed from the device to enable the medicament dosage in the next cartridge in the clip to be discharged into the next patient.

Preferably, each cartridge of the clip comprises a container, a dosage of medicament in the container, a hypodermic needle having a sharpened end for penetrating the muscle tissue of a patient and an opposite end through which the dosage of medicament is fed, means for sealingly containing the needle in a sterile condition in cooperating relation with the container and movable wall means at one end of the container operable when moved through a discharging stroke to cause the sharpened end of the needle to move outwardly out of sealingly contained relation and into the muscle tissue of a patient and the medicament dosage to move outwardly of the container into the opposite end of the needle and out of the sharpened end thereof into the muscle tissue of the patient.

Preferably, the medicament discharging device comprises a portable manually engageable housing structure defining a medicament cartridge receiving station, a plunger mounted in the housing structure for movement through the medicament cartridge receiving station in repetitive operative cycles each of which includes a discharging stroke in one direction and a return stroke in the opposite direction, manually actuatable means for effecting movement of the plunger through an operative cycle, and means on said housing structure detachably securing a clip in operative relation with the medicament cartridge receiving station of the housing structure such that when the manually actuatable means is manually actuated to effect movement of the plunger through an operative cycle with a medicament cartridge contained within the clip disposed within the cartridge receiving station the movable wall means thereof will be moved through a discharging stroke by said plunger during the discharging stroke thereof to cause the sharpened end of the needle to move outwardly out of sealingly contained relation and into the muscle tissue of a patient and the medicament dosage to move outwardly of the container into the opposite end of the needle and out of the sharpened end thereof into the muscle tissue of the patient.

It is a further object of the present invention to provide an expendable medicament cartridge containing clip of the type described and/or a medicament discharging device of the type disclosed which is effective in operation simple in construction and economical to manufacture.

These and other objects of the present invention will become more apparent during the course of the following detailed description and appended claims.

The invention may best be understood in conjunction with the accompanying drawings wherein illustrative embodiments are shown.

In the drawings:

FIGS. 4, 5 and 6 are schematic perspective views illustrating the steps undertaken by the discharging mechanism of the device in discharging the medicament dosage within the container of the cartridge and the removal of the container and needle from the cartridge receiving station after the medicament dosage therein has been discharged;

FIG. 8 is a vertical sectional view of the device and the clip shown in FIG. 7 similar to the vertical sectional view shown in FIG. 2;

FIG. 9 is a sectional view taken along the line 9—9 of FIG. 8;

FIG. 11 is a perspective view of still another medicament discharging device embodying the principles of the present invention having assembled in cooperating relation therewith a medicament cartridge containing clip of modified form embodying the principles of the present invention;

FIG. 12 is a front elevational view of the device and clip shown in FIG. 11;

FIG. 20 is an enlarged longitudinal sectional view of a cartridge of modified form embodying the principles of the present invention which may be utilized in lieu of any of the cartridges shown in the clips illustrated in FIGS. 1–19.

Referring now to FIGS. 1 through 6 of the drawings, there is shown therein an expendable medicament cartridge containing clip, generally indicated at 10, which embodies the principles of the present invention and is adapted to be cooperatively interengaged with a portable medicament discharging device, generally indicated at 12, embodying the principles of the present invention.

Figure 1:
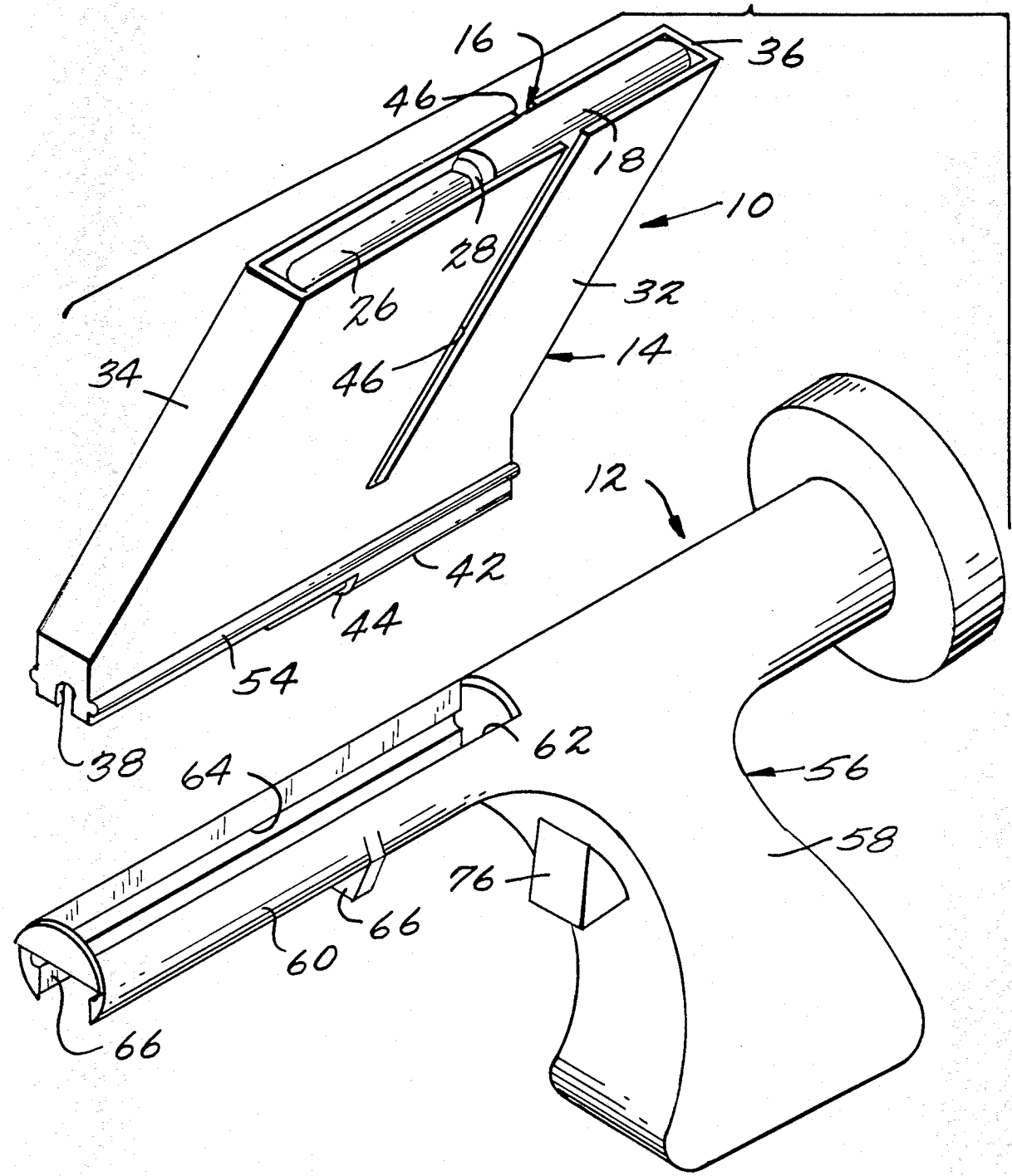
FIG. 1 is a perspective view of a medicament discharging device embodying the principles of the present invention and expendable medicament cartridge containing clip embodying the principles of the present invention used therewith, the clip being shown in exploded relation and having the end of the casing and the feeding spring removed for purposes of clearer illustration.
Figure 2:
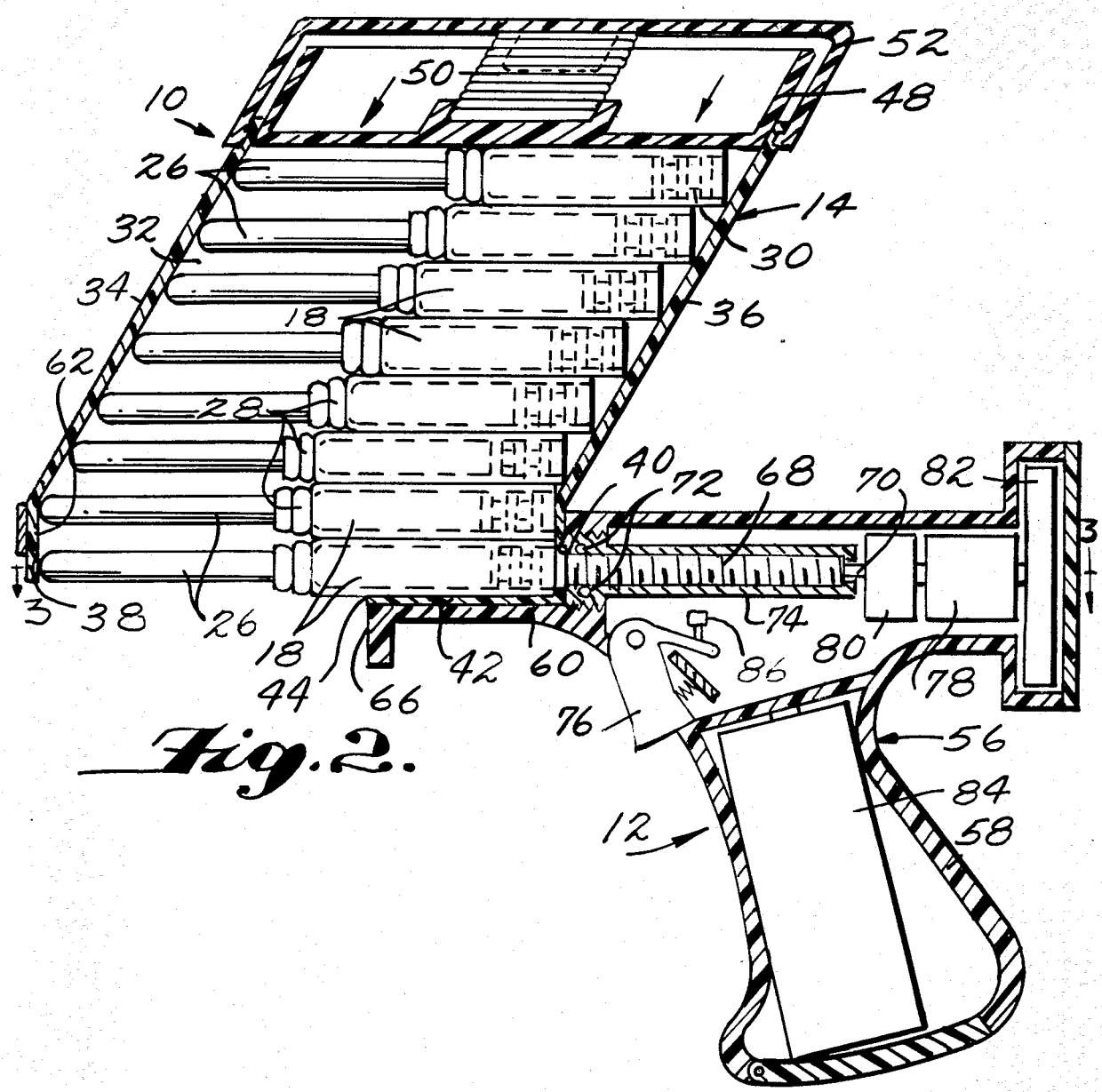
FIG. 2 is a vertical sectional view of the device shown in FIG. 1 with the clip operatively mounted therein.

As best shown in FIGS. 1 and 2, the clip 10 includes a boxlike casing structure, generally indicated at 14, for retaining a series of medicament cartridges, generally indicated at 16, in a unitary condition suitable for manual handling and interconnection with the medicament discharging device 12. As will become apparent hereinafter, each of the cartridges 16 may assume a variety of different configurations. In general, it can be stated that each cartridge includes a container 18, having a dosage of medicament 20 therein and a hypodermic needle 22 having a sharpened end 24 for penetrating the muscle tissue of a patient and an opposite end through which the dosage of medicament is received. Each cartridge 16 also includes means for sealingly containing the needle in a sterile condition in cooperating relation with the container, as, for example, an external resilient sheath 26.

Basically, the cartridges may be either one of two types depending upon the material of the medicament dosage and whether or not it can be safely stored in contact with the material of the hypodermic needle. In those cases where there is shelf life compatibility between the medicament and the needle material, the needle is interiorly sealingly retained within the container with the medicament surrounding the same. Where it is necessary to sealingly retain the medicament out of contact with the material of the needle, the needle is fixed in forwardly extending relation to the forward end of the container as by a ferrule assembly 28, such as shown in the FIGS. 1–6 and sealed by means of the exterior sheath 26. The ferrule assembly 28 between the needle and the forward end of the container includes in accordance with conventional practice a burstable diaphragm 29 (see FIG. 3) which accomplishes the sterile separation between the medicament and needle during the normal shelf life of the cartridge. The diaphragm 29 is capable of extending upon the application of pressure to the medicament and of engaging piercing elements (or the sharpened rear end of the needle) mounted within the ferrule assembly 28 which insure that the diaphragm will be broken to enable the medicament dosage to enter into the adjacent rear end of the needle passage. In this regard, see U.S. Pat. Nos. 3,380,449 and 3,391,695, the disclosures of which are hereby incorporated by reference into the present specification. Finally, each cartridge 16 also includes a moveable end wall, usually in the form of a piston 30 slidably sealingly mounted in the trailing end of the container 18.

The casing structure 14 may be formed of any suitable material by any suitable fabricating technique and, as shown, includes two molded plastic parts which together provide opposite side walls 32 of generally trapezoidal configuration and leading and trailing end walls 34 and 36, the major portion of which are disposed angularly along the leading and trailing edges of the trapezoidal shaped side wall 32 with the lower portions thereof extending vertically downwardly in parallel relation.

The lower portion of the leading end wall 34 is formed with a slot 38 which is of a size and shape to permit passage of the hypodermic needle 22 therethrough but to prevent the passage of the resilient sheath 26 enclosing the needle. The slot 38 is also open vertically downwardly to permit passage of the needle 22 laterally outwardly therefrom. The lower vertically extended portion of the trailing end wall 36 is formed with an opening 40, which is of a circular configuration having a diameter slightly less than the diameter of the cartridge container 18.

Figure 3:
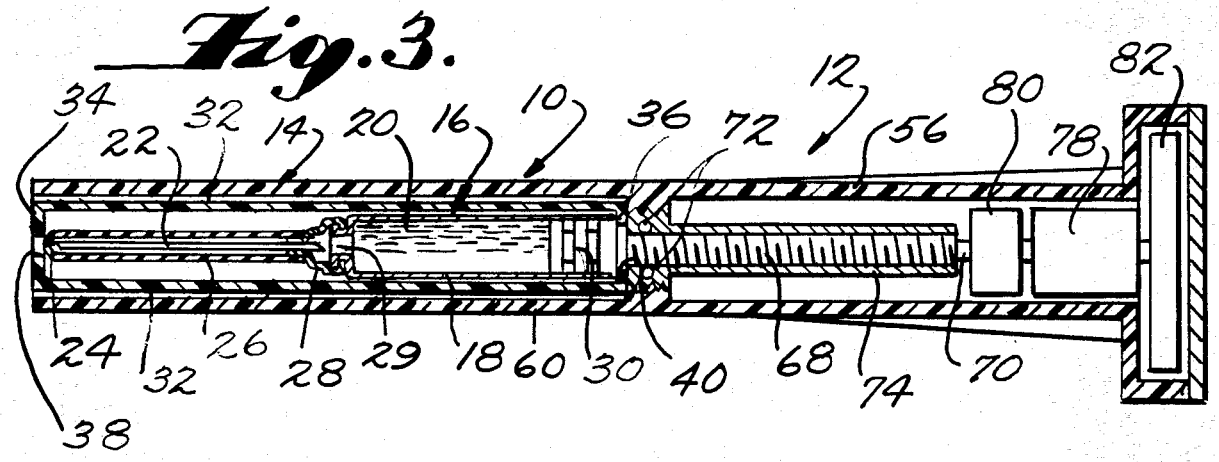
FIG. 3 is a sectional view taken along the line 3—3 of FIG. 2.

The series of cartridges 16 are disposed within the casing structure 14 in an inclined row formation with the containers 18 in parallel abutting relation and the needles 22 extending forwardly. The lowermost or leading cartridge 16 within the casing structure 14 is disposed directly below the adjacent cartridge and is retained within the casing structure 14 by a container engaging wall 42. As best shown in FIGS. 2 and 3, the container 18 of the leading or lowermost cartridge 16 is normally retained in engagement with the wall 42 in a position such that the rearward end of the container 18 and the associated piston 30 are aligned with the opening 40 and the sharpened end 24 of the associated needle 22 is aligned with the slot 38. The wall 42 extends forwardly from the trailing end wall 36 only partially toward the leading end wall 34 and terminates in a forwardly facing surface 44. The remainder of the casing structure 14 extending forwardly of the surface 44 between the lower edges of the side walls 32 up to the leading end wall 34 is open and is of a size sufficient to permit the passage of a container 18 of a discharged cartridge vertically downwardly therethrough.

The opposite side walls 32 of the casing structure 14 are formed with aligned slots 46 which extend in generally parallel relation with the inclined major portions of the end walls 34 and 36. Mounted for sliding movement within the slots 46 between the side walls 32 is a pusher member 48 positioned so that its lower surface engages the container 18 of the trailing or uppermost cartridge of the row formation of cartridges mounted within the casing structure 14. Pusher 48 is resiliently biased, as by a spring 50, to move the trailing cartridge engaged thereby in a direction toward the container engaging wall 42. Spring 50 is retained within the casing structure by a cap part 52 suitably fixed to the upper end of the side walls 32 and end walls 34 and 36.

Formed on the exterior surface of the side walls 32 along the lower marginal edge portions thereof is a pair of elongated ridges 54 which serve as releasable securing means for releasably securing the clip 10 in cooperative relation with the medicament discharging device 12. It will be understood that the ridge configuration is exemplary only and that any appropriate releasable latching means may be utilized to secure the releasable connection between the clip 10 and the device 12.

The medicament discharging device 12 shown in FIGS. 1-3 includes a housing structure 56 which is of a portable manually engageable construction of pistol shaped configuration. As shown, the housing structure includes a handle portion 58 having a barrel portion 60 extending forwardly from the upper end thereof. Preferably, the entire housing structure is of hollow configuration and the barrel portion 60 thereof is formed with an upper opening 62 of a size to receive the lower end portion of the clip 10 therein. Formed within the barrel portion is a pair of elongated longitudinal extending grooves 64 which are adapted to receive the ridges 54 and constitute the releasable securing means of the device 12. In addition to the opening 62, the barrel portion 60 also includes a lower opening 66 of a size corresponding to the size of the opening in the casing structure 14 of the clip permitting passage of a discharged cartridge 18 therethrough.

The interior of the barrel portion 60 defines within the housing structure 56 a cartridge receiving station through which a plunger 68 is moved in repetitive operative cycles. As shown, the plunger 68 is in the form of an elongated tubular member which is threaded exteriorly and formed with a constant non-circular interior cross-sectional configuration. The non-circular interior of the hollow member 68 is provided for the purpose of receiving a correspondingly shaped rotating element 70. In the embodiment shown the rotating element 70 has a square cross-sectional configuration which is uniform through its longitudinal extent and the interior of the member 68 has a mating or correspondingly shaped square cross-section. The plunger 68 is slidably mounted on the rotating member 70 so as to be rotated by the rotating element 70 while retaining the capability of relative longitudinal movement with respect to the rotating element 70. In order to cause the plunger 68 to move longitudinally in response to the rotational movement of the rotating element 70, the threaded exterior periphery of the plunger member 68 is mounted to engage a series of balls 72 suitably mounted in fixed position within the forward end of a mounting tube 74 disposed in surrounding relation with the plunger 68. Mounting tube 74 is suitably fixed within the housing structure 56 in a position aligned rearwardly of and in alignment with the cartridge receiving station within the barrel portion 60 of the housing structure 56.

In the embodiment shown in FIGS. 1-3 the device 12 includes a manually actuatable means in the form of a pivoted trigger 76 for actuating a direct current motor 78 for effecting rotation of the rotating element 70 in opposite directions. As shown, a speed reducing gear unit 80 is suitably mounted between the output shaft of the motor 78 and the rotating element 70. Also as shown, motor 78 has a fly wheel 82 connected therewith to assist in its operation. The motor 78 is energized by a battery pack 84 suitably mounted in the hollow handle portion 58 of the housing structure 56 under the control of a trigger switch 82 adapted to be actuated by a trigger 76. The switch 86, battery 84 and motor 78 are suitably connected within a conventional circuit (not shown) which includes reversing limiting switches. The arrangement is such that when the trigger 76 is in its extended normal storage position, plunger 68 will be in its retracted position as shown in FIGS. 2 and 3.

It will be understood that when it is desired to utilize the device 12 with a cartridge containing clip 10 secured in operative relation thereto the operator must first engage the forward end of the barrel portion 60 of the housing structure 56 in operative relation with the skin or clothing of the patient and specifically the muscle tissue which is to receive the injection. As soon as the operator has positioned the device 12 in operative relation with the patient as aforesaid, the operator simply depresses the trigger 76 to accomplish the injection procedure. When the operator actuates the trigger by depressing the same, switch 86 is actuated to energize the motor 78 causing the same, through speed reducer unit 80, to drive the rotating element 70 in a direction to turn the plunger 68 so that the turning movement thereof through the engagement of balls 72 with the exterior threads thereof causes the plunger to move longitudinally forwardly. As the forward end of the plunger member 68 moves forwardly it engages the rearward surface of the piston 30 of the leading cartridge disposed within the cartridge receiving station. Thereafter, the continued forward movement of the plunger 64 causes the entire cartridge 16 to move forwardly with the plunger until the forward end of the resilient sheath 26 engages the portion of the leading end wall 34 defining the slot 38 and its forward movement is stopped. As the plunger continues to move forwardly, the sharpened end 24 of the needle 22 moves through the end of the sheath 26 and outwardly into the muscle tissue of the patient (through any clothing covering the same). During this movement, the resilient sheath 26 is compressed against the portion of the leading end wall 34 against which it is engaged. This compression continues until there is sufficient resistance to the forward movement of the needle 22 and container 18 to retard and stop the movement of the same while permitting piston 30 to continue to move forwardly with the plunger 68. As best shown in FIG. 5, it will be noted that when container 18 reaches its stopped position, the rearward edge thereof is disposed forwardly of the surface 44.

The continued forward movement of the piston 30 with the plunger 68 while the container 18 is stopped pressurizes the medicament 20 sufficiently to expand the interior sealing diaphragm 29 (FIG. 3) and burst the same causing the medicament 20 to flow from the container 18 into the trailing end of the needle 22. As the piston 30 continues to move forwardly with the continued movement of the plunger 68 the medicament 20 within the container 18 is forced outwardly therefrom through the needle and into the muscle tissue of the patient. When the piston 30 reaches the forward end of the container 18 the limit switch (not shown) serves to de-energize motor 78 thus stopping the forward movement of plunger 68. Next, the operator withdraws the device 12 away from the patient which has the effect of removing the needle 22 from the patient's muscle tissue. The operator can now release the trigger 76 which causes motor 78 to be energized to rotate in the opposite direction. During the initial reverse movement, the clip spring 50 is of sufficient strength to cause the row of cartridges 16 to move the discharged lowermost cartridge slightly downwardly which motion is accommodated by the fact that the diameter size of the plunger 68 is less than the interior diameter of the container 18. Consequently, as the plunger 68 is retracted, the container 18 is moved into a lower position such that its rearward movement under the bias of the compressed resilient sheath 26 will cause the rearward edge of the container to engage the forwardly facing surface 44 thus stopping its rearward movement. In this way the container is retained in a position to move through the opening in the casing structure 14 of the clip 12 and the registering opening 66 in the barrel portion 60 of the housing structure 66 of the device 12. As soon as the rearward end of the plunger 68 moves rearwardly of the surface 44, the container is then biased by the clip spring 50 to move through the openings as aforesaid and out of retained relation within the clip 10. When the plunger 68 reaches its fully retracted position the other limit switch 86 (FIG. 2) serves to de-energize the motor 78 and recondition the circuit for another cycle which is initiated by depressing the trigger 76.

Referring now more particularly to FIGS. 7–10, there is shown therein a modified form of a medicament discharging device generally indicated at 112, embodying the principles of the present invention which is constructed to cooperatively receive a cartridge containing clip 10 of the type previously described. The device 112 includes a housing structure, generally indicated at 114, which like the housing structure 56 is manually engageable, portable, and of generally pistol-like configuration. As shown, the housing structure 114 includes a main handle portion 116 having a tubular portion 118 fixed to the upper end thereof and extending rearwardly thereof. The tubular portion 118 is formed with an interior chamber 120 within which is mounted a compressed $CO_2$ cartridge or container 122. Formed on the forward interior of the chamber 120 is a piercing element 124 of a configuration to engage and pierce the seal of the cartridge 122 in accordance with conventional procedures. The puncture of the seal is accomplished by engaging the cartridge 122 within the chamber and then turning a cap 126 which is threadedly mounted on the exterior rearward end of the tubular housing portion 118. As the cap 126 is turned the cartridge 122 is moved forwardly within the chamber to effect the piercing action. When the cap is fully tightened the forward end of the container sealingly engages an interior wall 128 within the tubular housing portion 118 which carries the piercing element 124. The interior wall 128 is rearwardly recessed to receive the forward end of the cartridge 122 and projects forwardly. Formed in the interior wall 128 is a central gas passage 130 which leads to a cavity 132 defining a rearwardly facing valve seat. A ball valve 134 is mounted within cavity 132 for movement forwardly into closing relation with the seat and rearward away from the seat. The arrangement is such that the gas pressure within the cartridge 122 which communicates with the cavity 132 normally biases the ball valve 134 into its forward closed position.

The housing structure 114 also includes a movable barrel and trigger part, generally indicated at 136. The housing part 136 includes a barrel portion 138 which has a construction similar to the barrel portion 60 of the device 12 shown in FIGS. 1–3.

Figure 7:
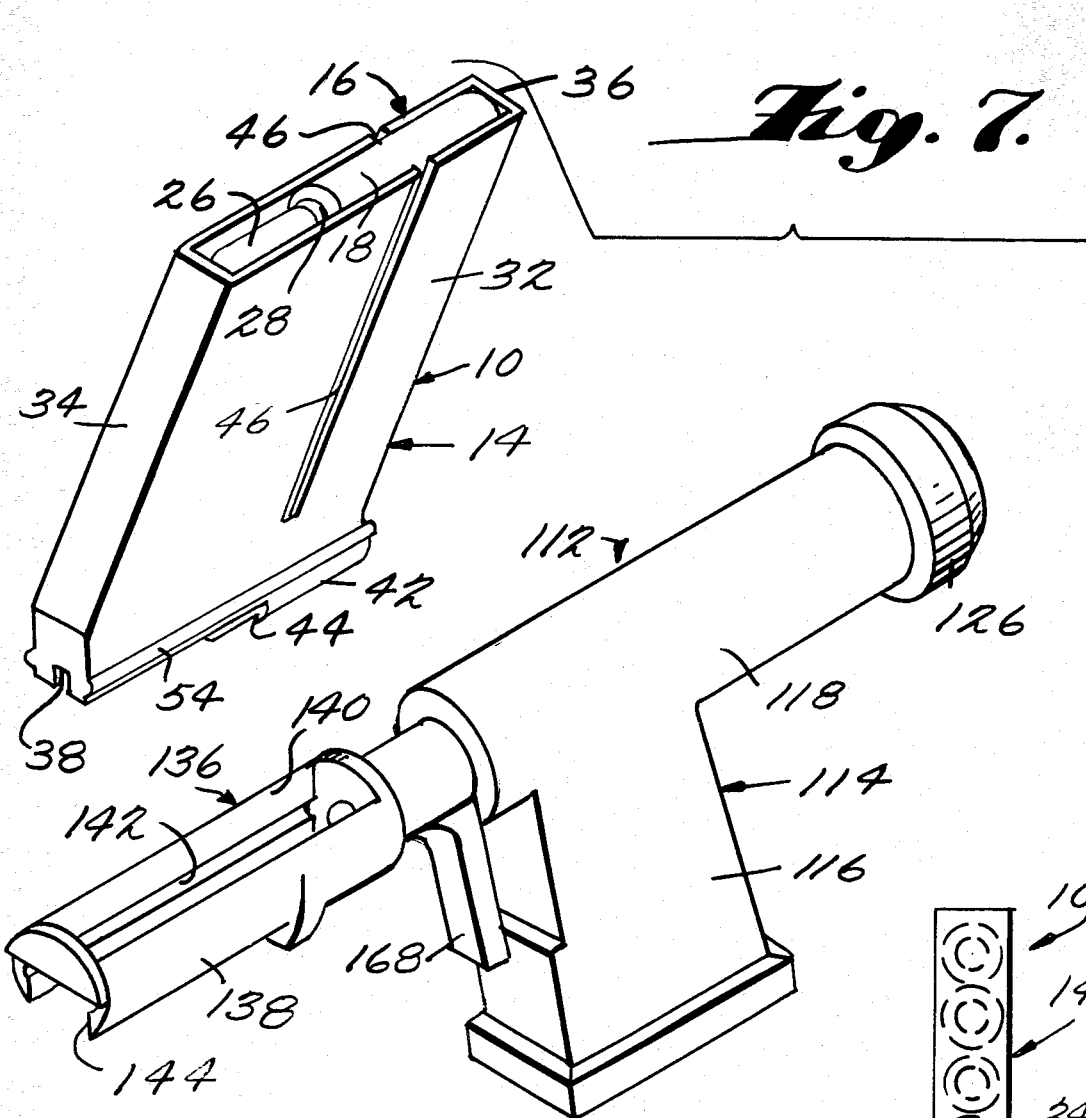
FIG. 7 is a view similar to FIG. 1 of a medicament discharging device of modified form embodying the principles of the present invention and a medicament cartridge containing clip similar to the clip shown in FIG. 1 used therewith.
Figure 10:
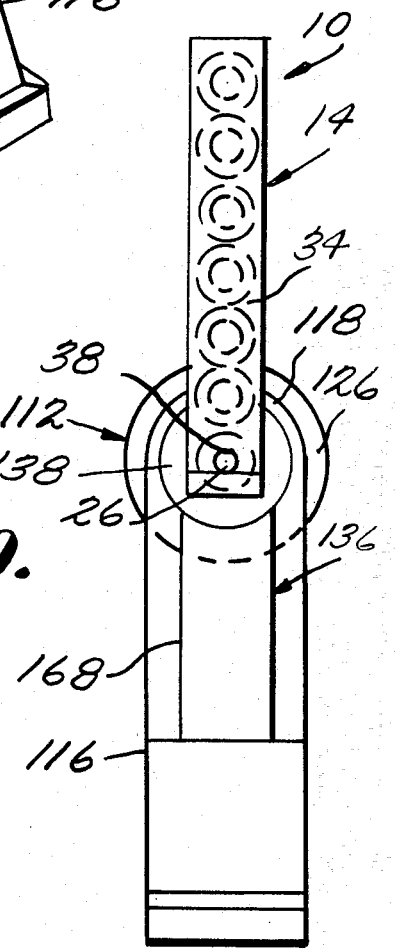
FIG. 10 is a front elevational view of the assembled device and clip shown in FIG. 7.

As can be seen from FIG. 7, the barrel portion 138 is formed with an upper opening 140 of a size to receive the lower end portion of the clip 10 therein. Formed within the barrel portion 138 is a pair of elongated longitudinally extended grooves 142 which are adapted to receive the ridges 54 of the clip 10 and constitute the releasable securing means of the device 114. As before the barrel portion 138 includes a low opening 144 of a size corresponding to the size of the opening in the casing structure 14 of the clip 10 permitting passage of a discharged cartridge 18 therethrough.

The barrel portion 138 defines within the housing structure 114 a cartridge receiving station through which a plunger 146 is moved in repetitive operative cycles. As best shown in FIGS. 8 and 9, the plunger 146 is in the form of an elongated rod constituting a piston rod fixed to and extending forwardly from a piston 148 slidably sealingly mounted within a bore 150 formed in the rearward portion of the moveable housing part 136 in alignment with the cartridge receiving station defined by the barrel portion 138. The plunger 146 is biased to move rearwardly through a return stroke into the rearward limiting portion shown in FIGS. 8 and 9 by a coil spring 152 which surrounds the plunger 146 and has its ends engaged respectively with the piston 148 and a snap ring 154 fixed within the forward end of the bore 150.

The rearward end of the bore 150 connects with an axial passage 156 extending through a rodlike projection 158 extending rearwardly from the central rearward surface of the moveable part 136. The moveable part 136 also includes a rearwardly extending sleeve portion 160 disposed in surrounding relation to the projection 158 and in sliding sealing relation with a cylindrical exterior surface 161 of the forwardly projecting portion of the interior wall 128 of the housing structure 114. Mounted in surrounding relation to the surface 161 against the interior wall 128 and the adjacent end of the sleeve portion 160 is a spring 162 which serves to bias the moveable housing part 136 into the forward limiting position shown in FIGS. 8 and 9. The forward limiting position is determined by the engagement of a set screw 164 within the rearward end of a slot 166 formed in the moveable part 136. The slot 166 extends forwardly sufficient to permit the moveable part 136 to be moved from the forward limiting position shown into a spaced rearward limiting position. The movement of the moveable housing part 136 into this position against the action of spring 162 is accomplished by the operator applying digital pressure to a trigger 168 which extends downward from the barrel portion 138 and forms an integral portion of the moveable part 136. It will be noted that the handle portion 116 of the housing structure 114 is hollow and provides an interior compartment 170 within which to store a spare or reserve $CO_2$ cartridge 122.

It will be understood that the cartridges of the clip 10 are discharged by operation of the device 112 in the same manner as previously described in connection with the device 12 shown in FIGS. 1 through 6. Thus, the device 112 accomplishes the discharge of the successive cartridges of the clip 10 by effecting movement of the plunger 146 through successive operating cycles each of which includes a forward medicament discharging stroke into the cartridge receiving station and a return stroke from a cartridge receiving station. The forward stroke is accomplished in response to the operator depressing the trigger 168 which has the effect of moving the movable housing part 136 from its forward limiting position shown in FIGS. 8 and 9 into its rearward limiting position against the bias of spring 162.

During the initial portion of this movement a radially extending exhaust port 172 formed in the sleeve portion 160 is covered by the peripheral surface 161. Next, the projecting portion 158 engages ball 134 and displaces the latter rearwardly away from its seat communicating the pressure within the chamber 132 with the passage 156 leading to the bore 150. The pressure within the bore 150 acts upon piston 148 and serves to move the same forwardly through a medicament discharging stroke. A vent hole 174 is provided in the movable part 136 in communication with the forward end of the bore 150. When the medicament discharging stroke has been completed resulting in the medicament being discharged into the patient, the needle is then removed as aforesaid. Thereafter, the return stroke is accomplished by the operator simply releasing the trigger 168 allowing the movable part 136 to move under the action of spring 162 from its rearward limiting position into the forward limiting position shown in FIGS. 8 and 9. During the initial portion of this movement, the projecting portion 158 moves forwardly allowing the ball 134 to be moved by the gas pressure within the chamber 132 back into its closed position in engagement with its valve seat. During the final part of this movement, the exhaust port 172 is moved out of closing relation with the surface 161, thus dumping to atmosphere the pressure acting on the piston 148 and permitting the spring 152 to move the piston 148 through its rearward return stroke. It will be noted that during this return stroke the gas within the bore 150 rearwardly of the piston is exhausted to atmosphere through the passage 156 and the exhaust port 172.

Referring more particularly to FIGS. 11 through 14 there is shown therein another form of clip, generally indicated at 210, embodying the principles of the present invention which is arranged to be cooperatively interengaged with a medicament discharging device, generally indicated at 212, which embodies the principles of the present invention.

The clip 210 is similar to the clip 10 previously described and includes all of the elements thereof with certain modifications provided for the purpose of cooperating with the device 212. The clip 210 includes a box-like casing structure 214 for retaining a series of medicament cartridges, generally indicated at 216, in a unitary condition suitable for manual handling and interconnection with the medicament discharging device 212. Each of the cartridges 216 is similar to a cartridge 16 of the type previously described in that it includes a container 218, having a dosage of medicament 220 therein and a hypodermic needle 222 having a sharpened end 224 for penetrating the muscle tissue of a patient opposite the end through which the medicament is received. A resilient sheath 226 covers the exterior of the needle and a ferrule assembly 228 serves to fixedly secure the opposite end of the needle to the forward end of the container 218. In addition to the above, each cartridge 216 also includes a coil spring 229 which surrounds the sheath 226 and has one end in engagement with the associated ferrule assembly 228 and a piston 230 in the rear end of the container 218.

The casing structure 214 is similar to the casing structure 14 previously described in that it includes opposite side walls 232 of trapezoidal configuration and leading and trailing end walls 234 and 236 extending angularly along the leading and trailing edges of the side walls. The leading portion of the leading end wall 234 is formed with an opening 238 rather than a slot, the opening 238 being of a size and shape to permit passage of a cartridge container 218 axially therethrough. Similarly, the corresponding leading end portion of the trailing end wall 236 is formed with an opening 240 which is of circular configuration having a diameter slightly less than the diameter of the cartridge container 218.

As before, the series of cartridges 216 is disposed within the casing structure 214 in an inclined row formation with the containers 218 in parallel abutting relation and the needles 222 extending forwardly. The leading cartridge 216 within the casing structure 214 is retained within the casing structure 214 by a container engaging wall 242 which extends completely between the leading and trailing end walls 234 and 236 respectively.

The portion of the casing structure 214 opposite from the wall 242 is closed by a wall 244 having an interior tubular portion 246 extending therefrom within which is mounted a spring 248. Spring 248 serves to resiliently bias a pusher 250 which is slidably mounted within the casing structure 214 in engagement with the trailing cartridge 216 of the series of cartridges in the inclined row formation.

Figure 13:
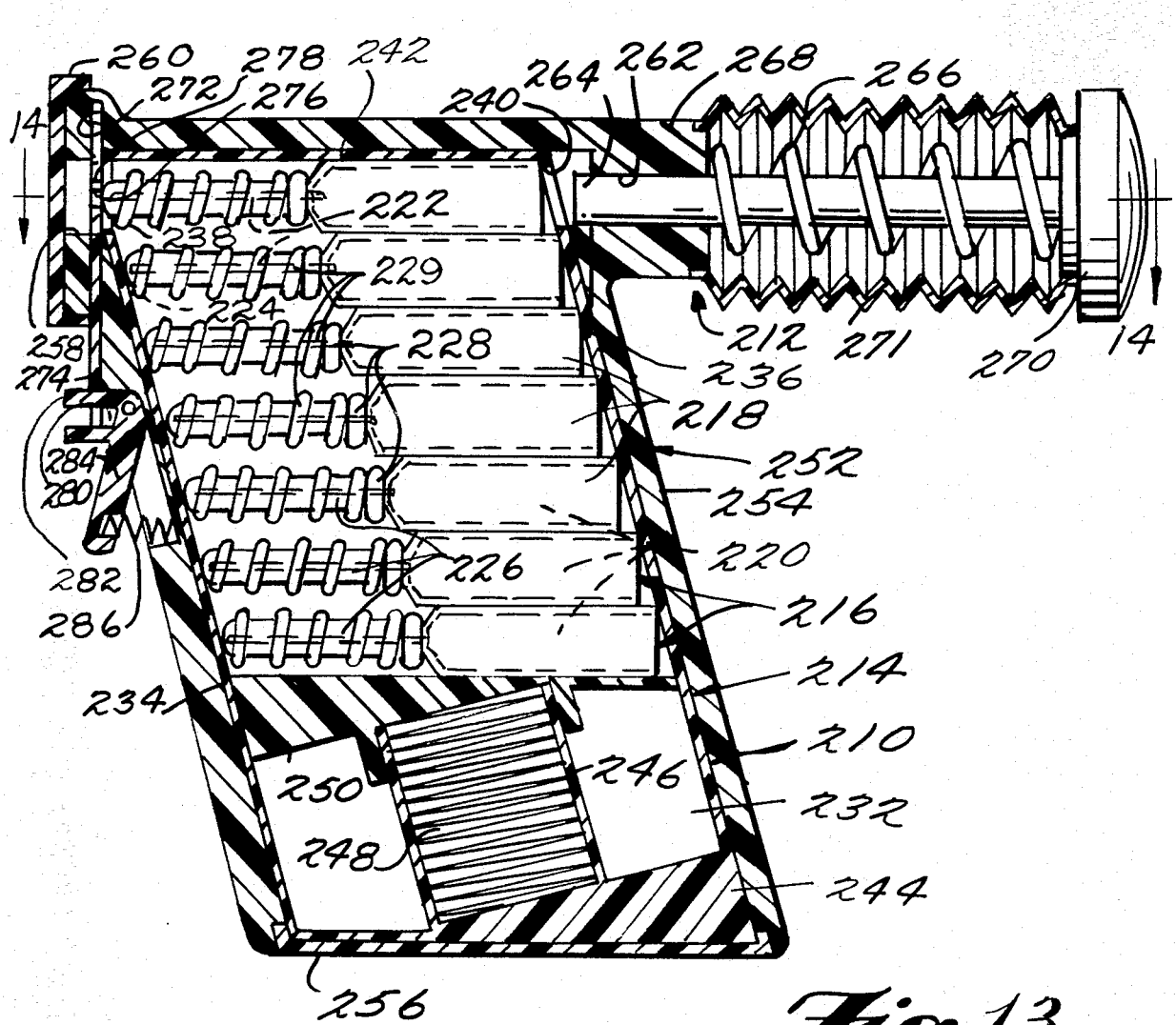
FIG. 13 is a vertical sectional view of the device and clip shown in FIGS. 11 and 12.
Figure 14:
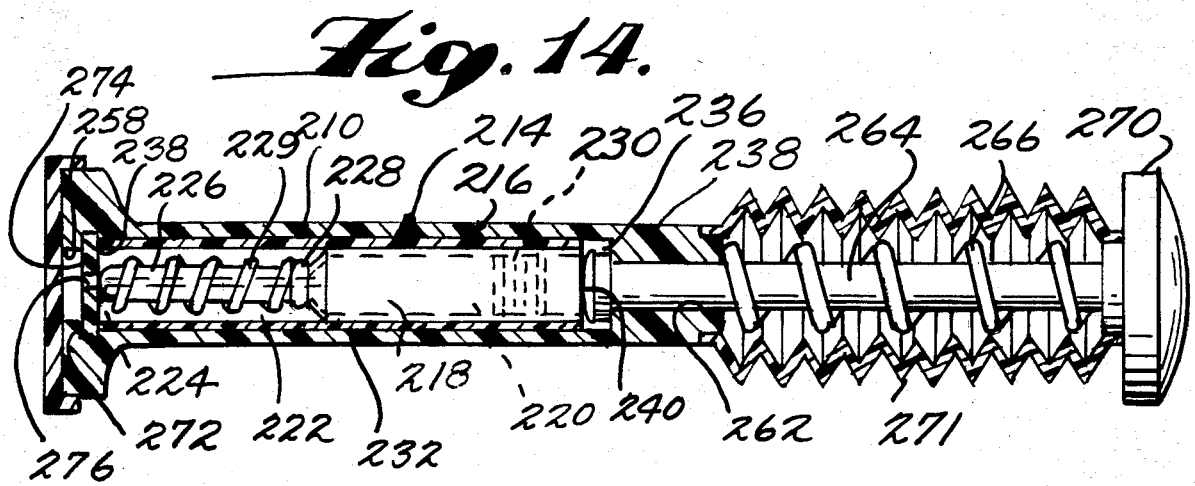
FIG. 14 is a sectional view taken along the line 14—14 of FIG. 13.

The medicament discharging device 212 includes a portable manually engageable housing structure 252 providing a hollow handle portion 254 configured to receive therein the clip 210. As best shown in FIG. 13, one end of the handle portion 254 includes a removable cover 256. When the cover is removed a used casing structure 214 can be removed from the handle portion and a new clip 210 mounted therein. After mounting a new clip 210 within the handle portion 254, the cover 256 is placed back into operative closing relation to the adjacent end of the handle portion.

The opposite end of the handle portion 254 leads to a cartridge receiving station within housing structure 252. The leading end of the cartridge receiving station is formed with an opening 258 of a size to permit passage of a cartridge container 218 axially therethrough. The exterior of the opening 258 is covered by a removable cap 260. The opposite end of the cartridge receiving station is formed with a bore 262 within which is slidably mounted a plunger 264. The plunger 264 is biased into a normal retracted position by means of a coil spring 266 which is disposed in surrounding relation to the plunger and has one end in engagement with the associated housing wall 268 and its opposite end affixed to a plunger head or knob 270. As shown, the spring 266 and exterior of the plunger 264 between the housing structure 252 and knob 270 is covered by a tubular bellows 271.

Formed in the portion of the housing structure defining the opening 258 is an elongated slot 272 which extends in a direction perpendicular to the axis of the plunger 268. Slidably mounted within the slot 272 is a plate 274 having a small opening 276 formed therein of a size to permit passage of a needle 222 therethrough but to prevent passage of the surrounding resilient sheath 226 therethrough and the associated surrounding coil spring 231. Plate 274 also includes a large opening 278 which is of a size similar to the openings 258 and 238 so as to permit the passage of a cartridge container 218 axially therethrough. The end of the plate 274 opposite from the end through which opening 278 is formed has an opening 280 formed therein through which an arm 282 of a trigger 284 extends. Trigger 284 is normally biased, as by a spring 286, into a position corresponding with the position of the plate 274 wherein the small opening 276 is aligned with the needle 222 of a cartridge 216 disposed within the cartridge receiving station. When trigger 284 is depressed arm 282 serves to move the plate 274 into a position wherein the large opening 278 is aligned with the openings 274 and 258.

In the use of the device 212, the operator first loads a clip 210 in the handle portion 254 by first removing cover 256 and replacing the same after the clip is mounted within the handle portion. After cap 260 has been removed, the operator grasps handle portion 254 and brings the leading end of the housing structure 252 into abutting engagement to the muscle tissue (or clothing covering the same) of the patient to be injected. The injection is accomplished by the operator manually engaging the knob or head 270 so as to move the plunger 274 longitudinally against the action of the spring 266 through a medicament discharging stroke into the cartridge receiving station. During this movement, the end of the plunger engages the piston 230 of the leading cartridge 216 and serves to move the entire cartridge forwardly. Immediately after this movement is commenced the sheath 226 engages the plate 274 and the sharpened end of the needle 222 moves through the small opening 276 and into the muscle tissue of the patient (through any clothing covering the same). During this movement both sheath 226 and the spring 231 are compressed. Continued movement of the plunger 264 through its medicament discharging stroke has the effect of discharging the medicament dosage 220 through the needle and into the patient as aforesaid. When the injection has been completed the needle 222 is withdrawn by moving the entire device 212 away from the patient. Releasing of the knob 270 enables the plunger 264 to move through a return stroke out of the cartridge receiving station under the action of spring 266. During this return stroke, the compression of spring 229 and resilient sheath 226 serve to return the discharged container 218 back into its initial position within the cartridge receiving station.

In order to discharge the spent cartridge from the casing structure 214, the operator then depresses trigger 284 which has the effect of moving plate 274 into a position wherein the large opening 278 is now aligned with opening 258. The operator can now engage knob 270 to move the plunger 264 through a second discharging stroke during which the plunger 264 engages the piston 230 of the discharged cartridge and moves the cartridge 216 outwardly through the openings 278 and 258. In this way the cartridge is discharged through the opening 258 after which the plunger 264 is allowed to move through a second return stroke under the action of spring 266 in response to the operator removing manual pressure from the knob 270.

Figure 15:
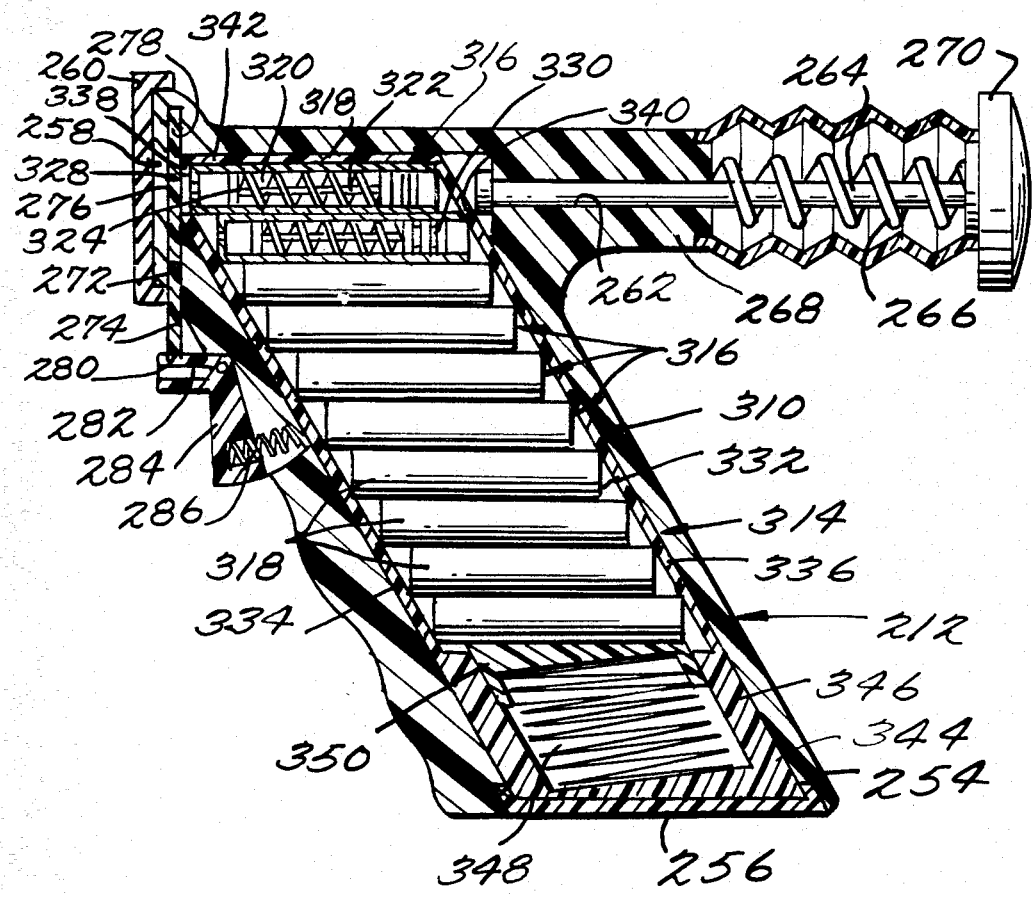
FIG. 15 is a view similar to FIG. 13 illustrating still another clip of modified form embodying the principles of the present invention.
Figure 16:
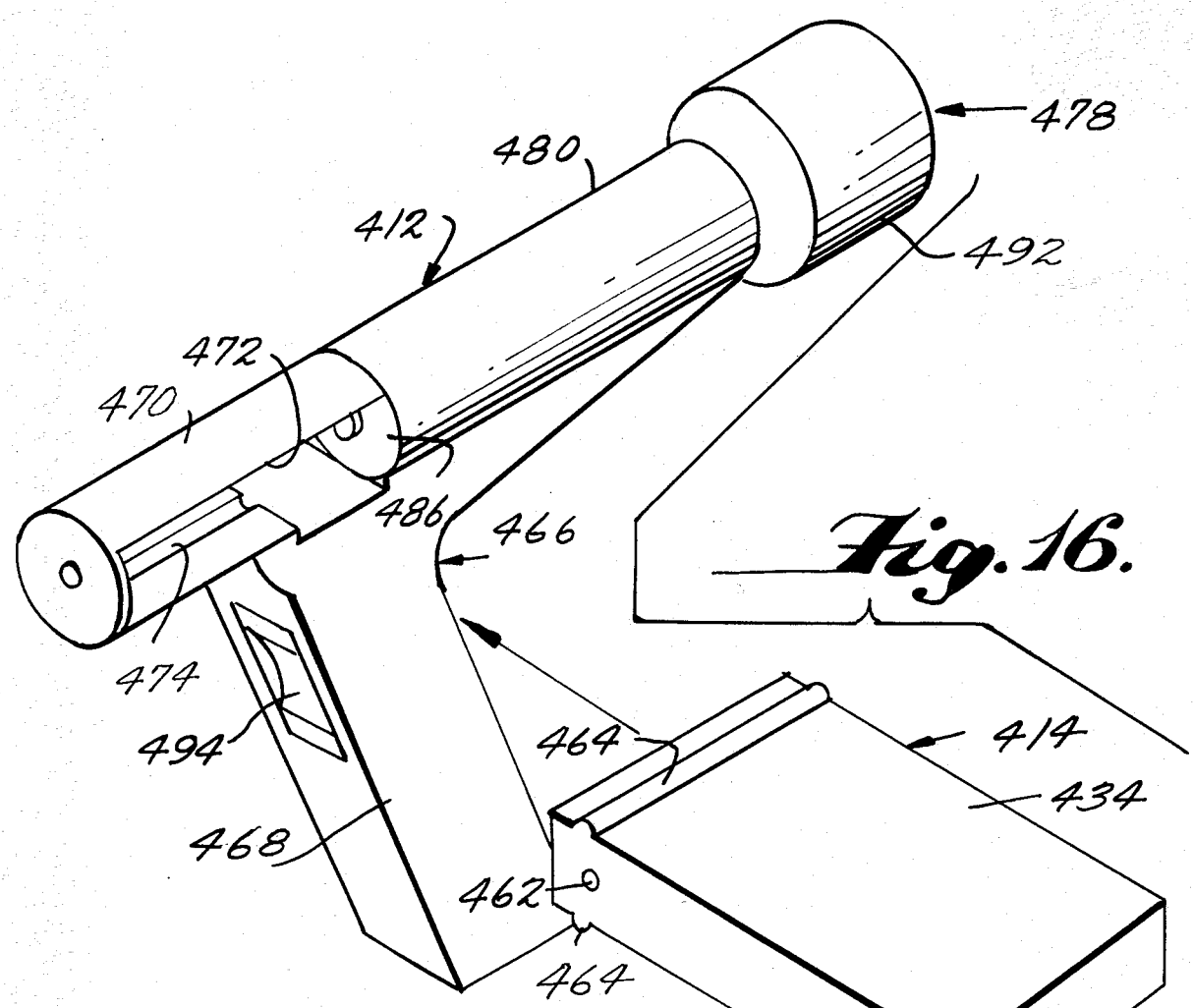
FIG. 16 is a view similar to FIG. 1 illustrating a medicament discharging device of still another form, embodying the principles of the present invention and still another medicament cartridge containing clip modification embodying the principles of the present invention.
Figure 17:
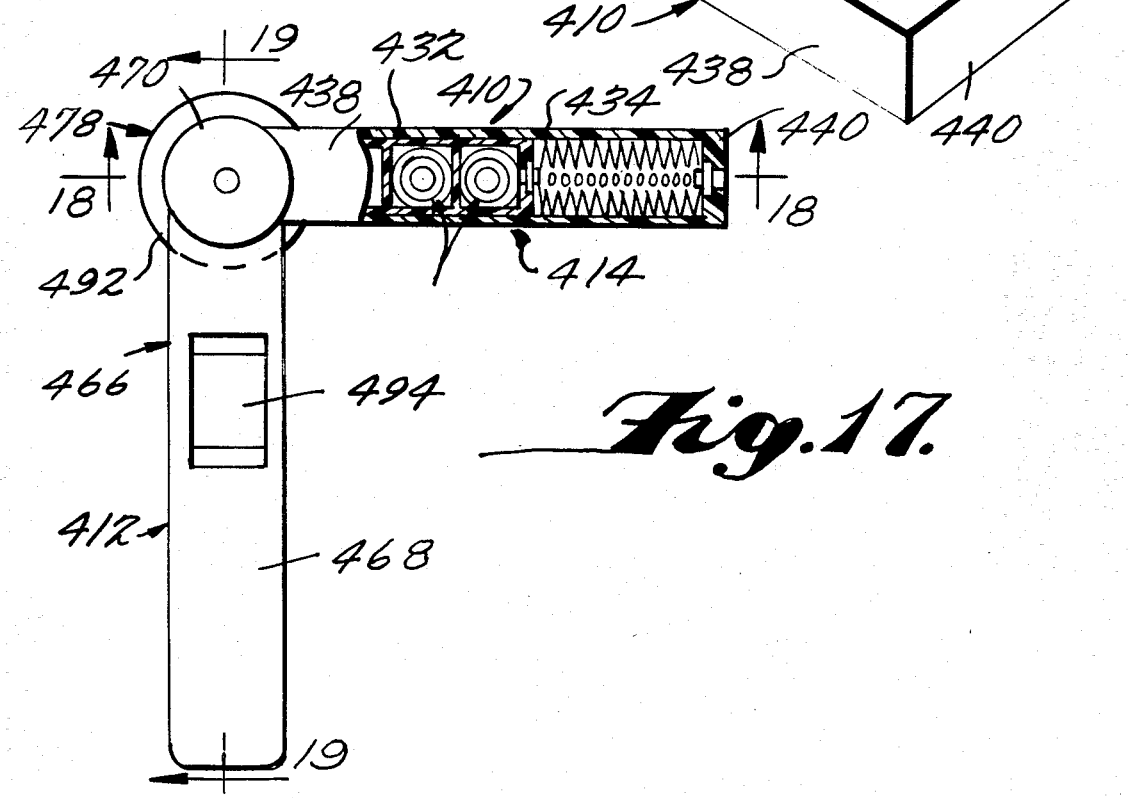
FIG. 17 is a front elevational view of the device and clip of FIG. 16 disposed in assembled cooperating relation with parts of the clip shown in section for purposes of clearer illustration.

FIG. 15 illustrates a clip 310 of modified form which is used with the device 212. The clip 310 is characterized by the provision of a casing structure 314 having a series of cartridges 316 therein each of which is of the interior needle type. As shown, each cartridge 316 includes a container 318 having a dosage of medicament 320 therein and a needle 322 disposed both within the container and within the dosage 320. The needle is sealed within the container by a resilient plug 324 which also serves to maintain the dosage therein and to receive the pointed end of the needle 322 as well as one end of an interior coil spring 326. As shown, each plug 324 is spaced rearwardly of a forward centrally apertured wall 328 in the forward end of the container 318. As before, a piston 330 is slidably sealingly retained in the rearward end of each container 318. The interior surface of each piston is disposed in engagement with the opposite end of the interior spring 326 and a rear end portion of the needle 322. The latter may include one or more laterally extending inlets leading to the hollow interior of the needle, see for example Sarnoff et al. U.S. Pat. No. 2,832,339, the disclosure of which is hereby incorporated by reference into the present specification.

The casing structure 314 is similar to the casing structure 214 previously described in that it includes opposite side walls 332 of trapezoidal configuration and leading and trailing end walls 334 and 336 extending angularly along the leading and trailing edges of the side walls. The leading portion of the leading end wall 334 is formed with an opening 338 of a size and shape to permit passage of a cartridge container 318 axially therethrough. Similarly, the corresponding leading end portion of the trailing end wall 336 is formed with an opening 340 which is of a circular configuration having a diameter slightly less than the diameter of the cartridge container 318.

As before, the series of cartridges 316 is disposed within the casing structure 314 in an inclined row formation with the containers 318 in parallel abutting relation and the needles 322 oriented forwardly. The leading cartridge 316 within the casing structure 314 is retained within the casing structure 314 by a container engaging wall 342 which extends completely between the leading and trailing end walls 334 and 336 respectively.

The portion of the casing structure 314 opposite from the wall 342 is closed by a wall 344 having an interior tubular portion 346 extending therefrom within which is mounted a spring 348. Spring 348 serves to resiliently bias a pusher 350 which is slidably mounted within the casing structure 314 in engagement with the trailing cartridge 316 of the series of cartridges in the inclined row formation.

Clip 310 is used in the device 212 in the same way as clip 210 with the interior spring 326 performing the same return function as the spring 229 except that the spring 326 serves to withdraw the needle 322 only back into the cartridge receiving station where the container 318 remains during the medicament discharging stroke of the plunger 264.

Referring now more particularly to FIGS. 16-19, there is shown therein still another embodiment of a medicament cartridge clip, generally indicated at 410, which is constructed so as to be interengaged with a medicament discharging device, generally indicated at 412, which embodies still another construction within the principles of the present invention. The clip 410 is shown as including an outer casing structure 414 within which is carried a series of medicament cartridges 416. The cartridges 416 are shown as being identical to the cartridges 216 described above in connection with the embodiment of FIGS. 11-14. It will be understood, however, that the clip 410 may embody interior needle cartridges such as the cartridges 316 shown in FIG. 15. The exterior needle type cartridges 416 shown, like the cartridges 216, each include a container 418, a medicament dosage 420, a needle 422, a needle enclosing resilient sheath 424, a sheath enclosing coil spring 426, a ferrule assembly 428 and a piston 430.

The cartridges 416 are mounted within the clip 410 in a straight row formation rather than an inclined row formation, as in many of the previous embodiments. Moreover, instead of being retained within the casing structure 414 for individual discharge from the casing after the medicament has been discharged from the cartridge, the entire series of cartridges is mounted within an indexable cell structure 432. The cell structure 432 is formed essentially of a one-piece molding providing a series of parallel through passages of a size to receive therein a cartridge 416 with the container 418 retained in guided sliding relation.

The casing structure 414 of the clip 410 includes the usual side walls 434 interconnected by a trailing wall 436 and a leading wall 438. A closure end wall 440 extends along one end of the casing structure and has internally engaged therewith a spring 442 which serves to resiliently bias the cell structure 432 containing the cartridges 416 in a direction toward the open opposite end of the casing structure.

Each cell of the cell structure 432 has formed in one wall thereof an indexing aperture 444 which is adapted to be engaged by an indexing mechanism, generally indicated at 446, carried by the casing structure 414. As exemplarily illustrated, the indexing mechanism 446 includes an indexing arm 448 which is pivoted exteriorly of one of the side walls 434 of the casing structure 414, as indicated at 450 in FIG. 19. The indexing arm includes an upstanding portion 452 which is biased to be engaged within an aligned one of the indexing openings 444 as by a hairpin spring 454 or the like. The indexing arm 448 extends rearwardly beyond the trailing wall 436 of the casing structure 414 and has a pivoted latch 456 mounted thereon. The latch is weighted so as to be biased into engagement with a stop or abutment 458 although it will be understood that rather than a weight bias the latch may be spring biased if desired.

Figure 18:
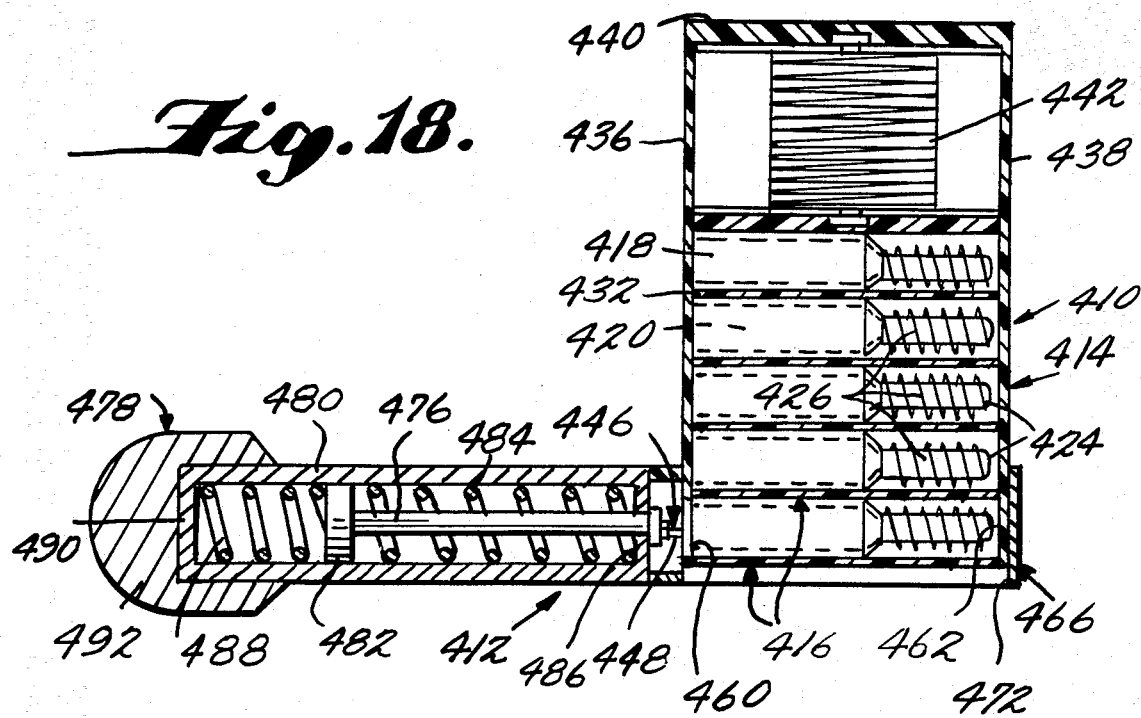
FIG. 18 is a sectional view taken along the line 18—18 of FIG. 17.
Figure 19:
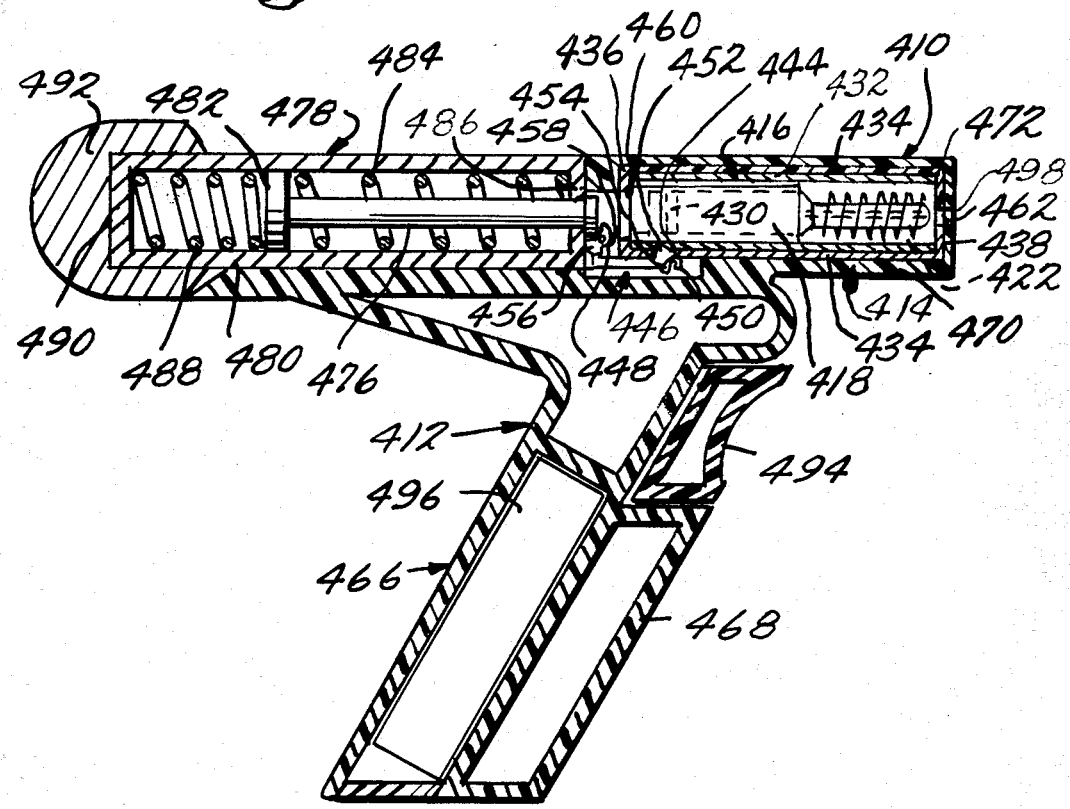
FIG. 19 is a sectional view taken along the line 19—19 of FIG. 17.

As best shown in FIGS. 18 and 19, the leading cartridge 416 is retained adjacent the open end of the casing structure 414 in a position such that the rearward end of the container 418 and the associated piston 430 are aligned with an opening 460 formed in the trailing wall 436 of a size slightly less than the piston size. The sharpened end of the associated needle 422 is is aligned with a small hole 462 formed in the leading wall 438 of a size permitting passage of the needle 422 therethrough but preventing passage of the sheath 424 and coil spring 426 therethrough.

Formed on the exterior surface of the side walls 434 along the open end marginal edge portions thereof is a pair of elongated ridges 464 which serve as releasable securing means for releasably securing the clip 410 in cooperative relation with the medicament discharging device 412. As before, it will be understood that the ridge configuration is exemplary only and that any appropriate releasable latching means may be utilized to secure the releasable connection between the clip 410 and the device 412.

The medicament discharging device 412 shown in FIGS. 16-19 includes a housing structure 466 which, as before, is of a portable manually engageable construction of pistol shaped configuration. As shown, the housing structure 466 includes a handle portion 468 having a barrel portion 470 extending forwardly from the upper end thereof. Preferably, the entire housing structure is of hollow configuration and the barrel portion 470 thereof is formed with a lateral through opening 472 of a size to receive the open end portion of the clip 410 therein. Formed within the barrel portion 470 is a pair of elongated longitudinal extending grooves 474 which are adapted to receive the ridges 464 and constitute the releasable securing means of the device 412.

The interior of the barrel portion 470 defines within the housing structure 466 a cartridge receiving station through which a plunger 476 is moved in repetitive operative cycles. As shown, the plunger 476 forms a part of a heat actuated Nitinol plunger moving assembly, generally indicated at 478. As shown, the assembly 478 includes a tubular housing 480 which slidably receives a disc 482 fixed to the rear end of the plunger 476.

A return coil spring 484 serves to resiliently bias the plunger 476 into a rearward limiting position wherein an enlarged plunger head engages an apertured front wall 486 of the tubular housing 480. Mounted within the rearward end of the tubular housing 480 is a coil of Nitinol material 488. Whereas coil spring 484 has one end engaged with the disc 482 and the opposite end engaged with the apertured end wall 486, the coil of Nitinol 488 has one end engaged with the disc 482 and the opposite end engaged with an imperforate end wall 490 at the rear of the tubular housing 480. The end wall 490 and the adjacent portion of the tubular housing 480 is surrounded by a heating element 492. The energization of the heating element 492 is under the control of a digitally actuated trigger 494 suitably mounted in the handle portion 468 of the housing structure 466. The handle portion 468 also serves to removably house a battery 496 which constitutes the energy source for actuating the heating element 492. It will be understood that a suitable switch circuit (not shown) is provided to accomplish the energization under the control of the trigger 494.

As is well known, Nitinol metal is a metal alloy having heat activated memory which can be cycled through its memory configuration through narrow temperature ranges. When the operator digitally presses the trigger 494, electrical energy from the battery 496 heats the element 492 which, in turn, raises the temperature of the Nitinol coil 488 and causes the same to expand moving the disc 482 forwardly against the action of the spring 484. The forward movement of the disc 482 carries with it the plunger 476.

It will be noted that during the initial portion of the movement of the plunger the enlarged head thereof will engage the pivoted latch 456 which simply pivots in a clockwise direction, as viewed in FIG. 19, to allow the plunger to pass in response to the movement of the plunger thereby. As the plunger moves past the pivoted latch 456, the latter is biased to move in a counterclockwise direction, as viewed in FIG. 19, back into the position shown which is disposed in the path of movement of the enlarged head of the plunger 476. As the plunger continues its forward movement the enlarged head thereof engages the piston 430 of the cartridge 412 disposed within the cartridge receiving station of the housing structure 466 of the device 412. The continued forward movement of the plunger effects the discharge of the medicament in a manner similar to that described above in connection with the embodiment of FIGS. 11-14. In this regard it will be noted that the end wall of the barrel portion 468 is formed with a small opening 498 which is aligned with the opening 462 of the casing structure of the clip 410.

After the medicament has been discharged into the patient as aforesaid and the needle removed, the operator releases trigger 494 which de-energizes heating element 492 allowing the temperature transmitted to the Nitinol coil 488 to reduce. As the temperature recedes the plunger 476 is moved through a return stroke by the action of the return spring 484. Toward the end of the return stroke, the enlarged head of the plunger 476 engages the pivoted latch 456 which cannot pivot about its pivot in a counterclockwise direction as viewed in FIG. 19 due to the engagement of the abutment 458. Consequently, the engagement causes the entire indexing arm 448 to pivot in a counterclockwise direction against the action of spring 454 about pivot 450 thus disengaging the projecting portion 452 from the opening 444 in the leading cell of the cell structure 432 and allowing the spring 442 to move the cell structure 432 outwardly through the open end of the casing structure 414. Immediately after the disengagement of the projecting portion 452 from the opening 444 the enlarged head of the plunger 476 moves rearwardly out of engagement with the pivoted latch 456 allowing the indexing arm 448 to be biased upwardly by the spring 454. Consequently as the cell structure 432 moves outwardly under the action of the spring 442 into a position wherein the indexing opening 444 of the next cell reaches the position of the projecting portion 452, the latter is biased to move into the opening, thus preventing further outward movement of the cell structure and positioning the next cartridge 416 into the cartridge receiving station of the device 412. It will be noted that the leading discharged cartridge is retained within the leading cell in its discharged condition.

Referring now more particularly to FIG. 20, there is shown therein another embodiment of a cartridge, generally indicated at 516, which embodies the principles of the present invention and can be utilized in lieu of the cartridges 316 in the clip 310 or the cartridges 416 in the clip 410. The cartridge 516 is similar in construction to the cartridge construction previously described in that it includes a container, generally indicated at 518; a medicament dosage 520 within the container; a hypodermic needle 522 within the container; and a movable end wall structure, generally indicated at 524.

The cartridge 516 differs from the previously described embodiments in the construction of the container 518 and movable end wall structure 524. As shown, the container 518 is formed of a plastic molding which includes a disc-shaped forward end wall 526 and a peripheral end wall made up of a series of annular bellows 528. The movable end wall structure 524 is preferably of a relatively stiff or rigid construction. As shown, the rearward end wall structure is a laminate including an inner disc of metal 530 and an outer disc of plastic material 532 which is sealed both to the disc 530 and to the adjacent end of the peripheral wall 528.

While it is within the contemplation of the construction of the cartridge 516 to provide a simple one-way connection between the movable end wall 524 and the needle 522 (see, for example, U.S. Pat. No. 3,318,021), preferably the remote end of the hypodermic needle opposite from the sharpened end 534 thereof is fixed to the movable end wall 524. An exemplary connection is shown in FIG. 20 as embodying a bore 536 in the central portion of the inner metal disc 530 which receives the remote end of the hypodermic needle 522 with a press fit. In order to communicate the interior of the hypodermic needle 522 at its remote end with the medicament dosage 520 within the container 518, an elongated opening 538 is formed laterally therein. It will be understood that other connections between the remote end of the hypodermic needle 522 and the movable end wall structure 524 may be utilized. For example, see the constructions embodied in U.S. Pat. No. 2,832,339, the disclosure of which is hereby incorporated by reference into the present specification.

The plastic material utilized to form the end wall 526 and peripheral wall 520 of the container is a thermoplastic resinous material, preferably polyethylene. The end wall 526 of the thermoplastic resinous material is readily pierceable by the sharpened end 534 of the needle 522 when a forwardly directed force is applied to the movable end wall 524. The material as embodied in the peripheral wall with the annular bellows 528 provides sufficient flexibility to permit collapse of the annular bellows as the forwardly directed force is applied to the movable end wall structure 524. Moreover, the material of the peripheral wall is such that when the forwardly directed force on the movable end wall is released after a full discharge stroke, there is sufficient bias in the material to accomplish a substantial return stroke even with the needle 522 in the muscle tissue of the patient. It will be understood that the bias provided by the material may be augmented by a spring bias if desired. Such spring may either be imbedded in the peripheral wall or disposed within the medicament space defined by the container.

It thus will be seen that the objects of this invention have been fully and effectively accomplished. It will be realized, however, that the foregoing preferred specific embodiment has been shown and described for the purpose of illustrating the functional and structural principles of this invention and is subject to change without departure from such principles. Therefore, this invention includes all modifications encompassed within the spirit and scope of the following claims.

What is claimed is:

1. An expendable medicament cartridge containing clip for use with a portable medicament discharging device having a cartridge receiving station and a medicament discharging mechanism movable through successive cycles each of which includes a medicament discharging stroke through said cartridge receiving station when a medicament cartridge is positioned in said station, said clip comprising
   a series of medicament cartridges, each of said cartridges comprising
      a container,
      a dosage of medicament in said container,
      a hypodermic needle having a sharpened end for penetrating the muscle tissue of a patient and an opposite end through which the dosage of medicament is fed,
      means for sealingly containing said needle in a sterile condition in cooperating relation with said container, and
      means at one end of said container operable in response to a discharging stroke of said medicament discharging mechanism when in the cartridge receiving station thereof to cause the sharpened end of said needle to move outwardly out of sealingly contained relation and into the muscle tissue of a patient and said medicament dosage to move outwardly of said container into the opposite end of said needle and out of the sharpened end thereof into the muscle tissue of the patient,
   casing means for retaining said series of cartridges in a unitary condition suitable for manual handling and connection with said medicament discharging mechanism, and
   means operable when said casing means is connected with the discharging mechanism for enabling successive medicament cartridges retained in said casing means to be moved into the cartridge receiving station of the discharging mechanism.

2. A clip as defined in claim 1 wherein the needle of each cartridge has the opposite end thereof disposed in fixed relation to the other end of the container, said sterile condition containing means comprising a resilient sheath exteriorly covering the sharpened end and a substantial portion of the needle extending toward the opposite end thereof disposed in fixed relation to said container.

3. A clip as defined in claim 2 wherein said needle movement causing means includes a cylindrical piston slidably sealingly mounted in said one end of said container in communicating relation to the medicament in said container enagageable during a discharge stroke of said medicament discharging mechanism to sequentially effect (1) the outward movement of said needle in fixed relation with said container and (2) the movement of said medicament dosage outwardly of said container and the sharpened end of said needle, said casing means having means for preventing outward movement of said resilient sheath during movement (1) and for preventing outward movement of said sheath, said needle and said container during movement (2).

4. A clip as defined in claim 3 wherein each cartridge includes diaphragm means disposed interiorly between the fixed ends of said needle and container for sealing said medicament dosage from the opposite end of said needle and for expanding outwardly during the initial portion of movement (2) and means for insuring that said diaphragm bursts when expanded outwardly so as to communicate the medicament dosage with the opposite end of said needle during the remaining portion of movement (2).

5. A clip as defined in claim 3 wherein each cartridge includes a coil spring surrounding said resilient sheath operable to be compressed with said sheath during movement (1).

6. A clip as defined in claim 3 wherein said sheath movement preventing means includes a fixed wall having a slot therein of a size and shape to permit (1) said needle to move axially outwardly therethrough sharpened end first from a position in which the sharpened end of the needle is spaced axially inwardly therefrom while preventing said sheath movement and (2) said needle to move laterally therefrom after having moved axially therethrough as aforesaid in (1), said casing also being open laterally in the same direction as said slot at a position axially inwardly thereof to an extent sufficient to permit said container to move laterally from said casing means in conjunction with the lateral movement of said needle from said slot after said medicament discharging mechanism has been moved through a return stroke following the discharging stroke thereof.

7. A clip as defined in claim 6 wherein said cartridge movement enabling means includes guide means on said casing means for guiding successive cartridges laterally into said cartridge receiving station in a direction corresponding to the lateral direction of said slot and spring means for resiliently urging successive cartridges to move into said cartridge receiving station and the container and needle of the cartridge in said cartridge receiving station to undertake the aforesaid lateral movements during the associated return stroke of the medicament discharging mechanism.

8. A clip as defined in claim 7 wherein said casing means includes a container engaging surface facing toward said slot and spaced axially inwardly therefrom a distance sufficient to engage the one end of a container during the return stroke of said medicament discharging mechanism so as to prevent a return movement of said container with the return stroke of said medicament discharging mechanism.

9. A clip as defined in claim 1 wherein the needle of each cartridge is disposed within said container, said sterile condition containing means including a pierceable wall at the other end of said container, said needle movement causing means comprising a movable wall at said one end of the container sealingly mounted for movement toward and away from said pierceable wall engageable during a discharge stroke of said medicament discharging mechanism to simultaneously effect (1) the outward movement of said needle in piercing relation through said pierceable wall and (2) the movement of said medicament dosage outwardly of said container and the sharpened end of said needle.

10. A clip as defined in claim 9 wherein said container comprises an open ended cylinder of rigid material, said pierceable wall comprising a plug of resilient material mounted within the open other end of said cylinder, said movable wall comprising a cylindrical piston slidably sealingly mounted within the open one end of said cylinder, said medicament dosage being disposed within said cylinder between said pierceable wall and said piston.

11. A clip as defined in claim 10 wherein the opposite end of said needle is enlarged laterally and disposed in engagement with said piston, said needle having a lateral inlet adjacent the laterally enlarged end thereof.

12. A clip as defined in claim 11 wherein each cartridge includes a coil spring surrounding said needle operable to be compressed between said pierceable wall and said piston during said simultaneous movements (1) and (2).

13. A clip as defined in claim 10 wherein said cartridge movement enabling means comprises guide surfaces on said casing means for retaining said series of cartridges in a row formation with the containers thereof disposed in parallel relation and the needles thereof pointing in the same direction and spring means acting between said casing means and the cartridge in said row formation remote from said cartridge receiving station for resiliently biasing the entire row formation of cartridges to move in a direction such that the cartridge in the row adjacent the cartridge in said cartridge receiving station is moved into said cartridge receiving station after the medicament dosage within the container of the cartridge within the cartridge receiving station has been discharged and the associated container and needle have been removed from the cartridge receiving station.

14. A clip as defined in claim 9 wherein said container comprises a cylindrical bellows of flexible material, said pierceable wall being fixed to the other end of said cylindrical bellows, said movable wall being fixed to said one end of said cylindrical bellows, said medicament dosage being disposed within said cylindrical bellows between said pierceable wall and said movable wall.

15. A clip as defined in claim 14 wherein the opposite end of said needle is enlarged laterally and disposed in engagement with said movable wall, said needle having a lateral inlet adjacent the laterally enlarged end thereof.

16. A clip as defined in claim 15 wherein said cartridge movement enabling means comprises guide surfaces on said casing means for retaining said series of cartridges in a row formation with the containers thereof disposed in parallel relation and the needles thereof pointing in the same direction and spring means acting between said casing means and the cartridge in said row formation remote from said cartridge receiving station for resiliently biasing the entire row formation of cartridges to move in a direction such that the cartridge in the row adjacent the cartridge in said cartridge receiving station is moved into said cartridge receiving station after the medicament dosage within the container of the cartridge within the cartridge receiving station has been discharged and the associated container and needle have been removed from the cartridge receiving station.

17. A clip as defined in claim 1 wherein said cartridge movement enabling means comprises guide surfaces on said casing means for retaining said series of cartridges in a row formation with the containers thereof disposed in parallel relation and the needles thereof pointing in the same direction and spring means acting between said casing means and the cartridge in said row formation remote from said cartridge receiving station for resiliently biasing the entire row formation of cartridges to move in a direction such that the cartridge in the row adjacent the cartridge in said cartridge receiving station is moved into said cartridge receiving station after the medicament dosage within the container of the cartridge within the cartridge receiving station has been discharged and the associated container and needle have been removed from the cartridge receiving station.

18. A clip as defined in claim 17 wherein said cartridge movement enabling means further includes a cartridge holder mounted within said casing means for indexed movement by said spring means, said holder including a series of side-by-side tubular cartridge holding cells open at opposite ends.

19. A clip as defined in claim 13 wherein said cartridge movement enabling means further includes a cartridge holder mounted within said casing means for indexed movement, said holder including a series of side-by-side tubular cartridge holding cells open at opposite ends.

20. A medicament discharging device for use with an expendable medicament cartridge containing clip in which each cartridge includes a container, a dosage of medicament in said container, a hypodermic needle having a sharpened end for penetrating the muscle tissue of a patient and an opposite end through which the dosage of medicament is fed, means for sealingly containing said needle in a sterile condition in cooperating relation with the container and movable wall means at one end of the container operable in response to a discharging stroke operable when moved through a discharging stroke to cause the sharpened end of said needle to move outwardly out of sealingly contained relation and into the muscle tissue of a patient and the medicament dosage to move outwardly of the container into the opposite end of the needle and out of the sharpened end thereof into the muscle tissue of the patient, said medicament discharging device comprising
a portable manually engageable housing structure defining a medicament cartridge receiving station,
a plunger mounted in said housing structure for movement through said medicament cartridge receiving station in repetitive operative cycles each of which includes a discharging stroke in one direction and a return stroke in the opposite direction,
manually actuatable means for effecting movement of said plunger through an operative cycle, and
means on said housing structure for detachably securing a clip of the type described in operative relation with the medicament cartridge receiving station of said housing structure such that when said manually actuatable means is manually actuated to effect movement of said plunger through an operative cycle with a medicament cartridge contained within said clip disposed within said cartridge receiving station the movable wall means thereof will be acted upon by said plunger during the discharging stroke thereof to cause the sharpened end of the needle to move outwardly out of sealingly contained relation and into the muscle tissue of a patient and the medicament dosage to move outwardly of the container into the opposite end of the needle and out of the sharpened end thereof into the muscle tissue of the patient.

21. A medicament discharging device as defined in claim 20 wherein said plunger includes an elongated plunger rod having one end adapted to move through said medicament cartridge receiving station and an opposite end formed with an enlargement thereon, said plunger movement effecting means including a return coil spring surrounding said plunger rod and acting between said enlargement and said housing structure for resiliently biasing said plunger to move through said return stroke.

22. A medicament discharging device as defined in claim 21 wherein said enlargement is a manually engageable knob disposed exteriorly of said housing structure.

23. A medicament discharging device as defined in claim 21 wherein said enlargement is a piston slidably mounted within a cylinder within said housing structure.

24. A medicament discharging device as defined in claim 23 wherein said piston is pneumatically sealingly mounted within said cylinder, said plunger movement effecting means further including a container having a source of gas under pressure therein and valve means for communicating said source of gas pressure with said cylinder to effect a discharging stroke of said piston and plunger through the action of fluid pressure on said piston and for exhausting said fluid pressure from said cylinder to enable said return spring to effect the return stroke.

25. A medicament discharging device as defined in claim 24 wherein said plunger movement effecting means further includes a manually engageable trigger structure and means for actuating said valve means to communicate said source of gas under pressure with said cylinder in response to a movement of the trigger under digital pressure and for exhausting said cylinder in response to the digital release of said trigger.

26. A medicament discharging device as defined in claim 25 wherein said valve means includes a one-way ball valve normally closing off communication of said source of gas under pressure and movable into an open position to communicate the source of gas under pressure with said cylinder and a vent valve normally open when said ball valve is closed movable into a closed position when said ball valve is moved into its open position.

27. A medicament discharging device as defined in claim 23 wherein said piston is slidably mounted within said cylinder in an intermediate position therein, said plunger movement effecting means further including a Nitinol coil in said cylinder and means for heating said Nitinol coil, said Nitinol coil being mounted within said cylinder so as to act between said piston and said housing structure when heated by said heating means to move the piston and plunger through a discharging stroke.

28. A medicament discharging device as defined in claim 27 wherein said heating means includes a heating element surrounding said Nitinol coil, a battery for energizing said heating element and a trigger for actuating a switch controlling the energization of said heating element by said battery.

29. A medicament discharging device as defined in claim 20 wherein said plunger movement effecting means comprises a reversible electric motor carried by said housing structure, a speed reducing unit drivingly connected with said electric motor, said speed reducing unit having an output shaft and means operable in response to the turning of said output shaft in one direction for effecting the discharge stroke of said plunger and to the turning of said output shaft in the opposite direction for effecting said return stroke.

30. A medicament discharging device as defined in claim 29 wherein said last-mentioned means comprises exterior threads on said plunger, ball means carried by said housing for engaging said exterior threads, said output shaft having a non-circular cross-sectional configuration, said plunger having an exterior cross-sectional configuration mating with the exterior cross-sectional configuration of said output shaft so as to permit relative longitudinal movement of said plunger with respect to said output shaft and to insure rotational movement therewith.

31. A medicament discharging device as defined in claim 20 wherein said housing structure includes a member mounted for movement between a medicament discharging position and a cartridge discharging position, said member being disposed in the outward path of movement of a cartridge whose movable wall means is engaged by said plunger during the discharging stroke thereof and having an opening therein of a size to permit the passage of the needle of the cartridge therethrough and to prevent the passage of the cartridge container therethrough, said member when in said cartridge discharging position permitting movement of the container of a discharged cartridge outwardly from said cartridge receiving station.

32. A medicament discharging device as defined in claim 31 wherein said housing structure includes a digitally engageable trigger mounted thereon for movement between first and second positions, and means for connecting said member with said trigger so that said member is moved into said cartridge discharging position when said trigger is moved into said second position and said member is moved into said medicament discharging position when said trigger is moved into said first position.

33. A medicament discharging device as defined in claim 32 wherein said trigger has spring means operatively connected therewith biasing the same into said first position and yielding in response to digital pressure on said trigger to permit movement thereof into said second position.

34. The combination of a medicament discharging device and an expendable clip containing a plurality of medicament cartridges, each of said cartridges comprising a container,
a dosage of medicament in said container,
a hypodermic needle having a sharpened end for penetrating the muscle tissue of a patient and an opposite end through which the dosage of medicament is fed,
means for sealingly containing said needle in a sterile condition in cooperating relation with the container and
movable wall means at one end of the container operable when moved through a discharging stroke to cause the sharpened end of said needle to move outwardly out of sealingly contained relation and into the muscle tissue of a patient and the medicament dosage to move outwardly of the container into the opposite end of the needle and out of the sharpened end thereof into the muscle tissue of the patient,
said medicament discharging device comprising
a portable manually engageable housing structure defining a medicament cartridge receiving station,
a plunger mounted in said housing structure for movement through said medicament cartridge receiving station in repetitive operative cycles each of which includes a discharging stroke in one direction and a return stroke in the opposite direction,
manually actuatable means for effecting movement of said plunger through an operative cycle, and
means on said housing structure detachably securing a clip in operative relation with the medicament cartridge receiving station of said housing structure such that when said manually actuatable means is manually actuated to effect movement of said plunger through an operative cycle with a medicament cartridge contained within said clip disposed within said cartridge receiving station the movable wall means thereof will be moved through a discharging stroke by said plunger during the discharging stroke thereof to cause the sharpened end of the needle to move outwardly out of sealingly contained relation and into the muscle tissue of a patient and the medicament dosage to move outwardly of the container into the opposite end of the needle and out of the sharpened end thereof into the muscle tissue of the patient.

35. The combination as defined in claim 34 wherein said housing structure includes a member mounted for movement between a medicament discharging position and a cartridge discharging position, said member being disposed on the outward path of movement of a cartridge whose movable wall means is engaged by said plunger during the discharging stroke thereof and having an opening therein of a size to permit the passage of the needle of the cartridge therethrough and to prevent the passage of the cartridge container therethrough, said member when in said cartridge discharging position permitting movement of the container of a discharged cartridge outwardly from said cartridge receiving station.

36. The combination as defined in claim 35 wherein said housing structure includes a digitally engageable trigger mounted thereon for movement between first and second positions, and means for connecting said member with said trigger so that said member is moved into said cartridge discharging position when said trigger is moved into said second position and said member is moved into said medicament discharging position when said trigger is moved into said first position.

37. The combination as defined in claim 36 wherein said trigger has spring means operatively connected therewith biasing the same into said first position and yielding in response to digital pressure on said trigger to permit movement thereof into said second position.

38. The combination as defined in claim 35 wherein the needle of each cartridge is disposed within said container, said sterile condition containing means including a pierceable wall at the other end of said container, said needle movement causing means comprising a movable wall at said one end of the container sealingly mounted for movement toward and away from said pierceable wall engageable during a discharge stroke of said medicament discharging mechanism to simultaneously effect (1) the outward movement of said needle in piercing relation through said pierceable wall and (2) the movement of said medicament dosage outwardly of said container and the sharpened end of said needle.

39. The combination as defined in claim 35 wherein the needle of each cartridge has the opposite end thereof disposed in fixed relation to the other end of the container, said sterile condition containing means comprising a resilient sheath exteriorly covering the sharpened end and a substantial portion of the needle extending toward the opposite end thereof disposed in fixed relation to said container.

40. The combination as defined in claim 34 wherein the needle of each cartridge has the opposite end thereof disposed in fixed relation to the other end of the container, said sterile condition containing means comprising a resilient sheath exteriorly covering the sharpened end and a substantial portion of the needle extending toward the opposite end thereof disposed in fixed relation to said container.

41. The combination as defined in claim 40 including spaced forward and rearward abutment surface means facing toward one another and lateral opening means within said forward abutment surface means and extending rearwardly to said rearward abutment surface means operable (1) during the discharging stroke of said plunger in engagement with the movable wall means of a cartridge in said cartridge receiving station to permit movement of the needle of said cartridge longitudinally therethrough while the longitudinal movement of said sheath is prevented by engagement with said forward abutment surface means and (2) during the subsequent return stroke of said plunger to allow a bias on the container of said cartridge in the lateral direction of said lateral opening means to cause a rearward edge of the cartridge container to engage said rearward abutment means to prevent further rearward movement thereof while said plunger is removed therefrom during the continued return stroke thereof so that the lateral bias on said cartridge container is operable to discharge the cartridge with the medicament discharged therefrom through said lateral opening means.

* * * * *